(12) United States Patent
Jakus et al.

(10) Patent No.: US 12,139,696 B2
(45) Date of Patent: Nov. 12, 2024

(54) BIOINTEGRATIVE IMPLANTABLE CELL ENCAPSULATION DEVICE AND SYSTEM

(71) Applicant: DIMENSION INX CORP., Chicago, IL (US)

(72) Inventors: Adam E. Jakus, Chicago, IL (US); Jonathon Burke, Elk Grove Village, IL (US); Henry Kim, Glenview, IL (US); Ramille N. Shah, Oak Brook, IL (US); Carolina I. Bohorquez Fuentes, Chicago, IL (US); Cole Johnson, Chicago, IL (US)

(73) Assignee: DIMENSION INX CORP., Chicago, IL (US)

( * ) Notice: Subject to any disclaimer, the term of this patent is extended or adjusted under 35 U.S.C. 154(b) by 0 days.

(21) Appl. No.: 18/235,091

(22) Filed: Aug. 17, 2023

(65) Prior Publication Data
US 2024/0060028 A1 Feb. 22, 2024

Related U.S. Application Data

(60) Provisional application No. 63/399,449, filed on Aug. 19, 2022.

(51) Int. Cl.
| | |
|---|---|
| C12M 1/12 | (2006.01) |
| A61L 27/22 | (2006.01) |
| A61L 27/38 | (2006.01) |
| A61L 27/54 | (2006.01) |
| A61L 27/56 | (2006.01) |

(Continued)

(52) U.S. Cl.
CPC ........... *C12M 25/16* (2013.01); *A61L 27/227* (2013.01); *A61L 27/3804* (2013.01); *A61L 27/3834* (2013.01); *A61L 27/54* (2013.01); *A61L 27/56* (2013.01); *B33Y 10/00* (2014.12);
(Continued)

(58) Field of Classification Search
CPC ...... A61K 9/0024; A61K 35/28; A61K 35/12; A61L 27/3633; A61L 27/38; A61L 27/3804; A61L 27/3834; A61L 27/18; A61L 27/3604; A61L 27/52; C12M 21/08;
(Continued)

(56) References Cited

U.S. PATENT DOCUMENTS

| | | |
|---|---|---|
| 9,327,448 B2 | 5/2016 | Shah et al. |
| 9,526,880 B2 | 12/2016 | So et al. |

(Continued)

OTHER PUBLICATIONS

International Search Report and Written Opinion for International Patent Application No. PCT/US2023/030458 dated Dec. 20, 2023, 12 pages.

*Primary Examiner* — Manuel A Mendez
(74) *Attorney, Agent, or Firm* — Hahn Loeser & Parks LLP

(57) ABSTRACT

The cell encapsulation system (CES) device is a device used for dermal, subdermal, muscle, tissue, or organ implantation into an individual (host) that is capable of being loaded with and carrying and containing exogenously introduced cells (encapsulated cells) that can produce relevant biochemicals (factors) and/or therapeutic molecules that can be transported to the host tissue while simultaneously not eliciting a significant host immune response (to the implanted device or to the encapsulated cells). The CES device provides a means of local and/or systemic, prolonged delivery of single or multiple factors and/or therapeutic molecules to alleviate, treat, or cure a variety of acute and chronic pathologies and ailments.

58 Claims, 21 Drawing Sheets
(11 of 21 Drawing Sheet(s) Filed in Color)

(51) Int. Cl.
  *B33Y 10/00* (2015.01)
  *B33Y 70/00* (2020.01)
(52) U.S. Cl.
  CPC .............. *B33Y 70/00* (2014.12); *C12M 25/14* (2013.01); *A61L 2300/62* (2013.01)
(58) Field of Classification Search
  CPC ........... C12M 25/16; A61F 2/022; A61F 2/02; C12N 5/0068; B33Y 10/00; B33Y 70/00
  See application file for complete search history.

(56) References Cited

U.S. PATENT DOCUMENTS

| | | |
|---|---|---|
| 10,236,528 B2 | 3/2019 | Jakus et al. |
| 10,272,179 B2 | 4/2019 | Martinson et al. |
| 10,350,329 B2 | 7/2019 | Shah et al. |
| 10,584,254 B2 | 3/2020 | Shah et al. |
| 10,793,733 B2 | 10/2020 | Shah et al. |
| 11,654,214 B2 | 5/2023 | Shah et al. |
| 2015/0125507 A1 | 5/2015 | Chen et al. |
| 2018/0085493 A1 | 3/2018 | Lee |
| 2019/0254959 A1 | 8/2019 | Tuch et al. |
| 2019/0328934 A1 | 10/2019 | D'Amour et al. |
| 2019/0343989 A1 | 11/2019 | Jakus et al. |
| 2020/0281987 A1 | 9/2020 | Agulnick et al. |
| 2020/0353129 A1 | 11/2020 | Jakus et al. |
| 2022/0233298 A1 | 7/2022 | Aghdasi et al. |
| 2022/0233299 A1 | 7/2022 | Bruhn et al. |
| 2022/0234006 A1 | 7/2022 | Bruhn et al. |
| 2022/0401630 A1 | 12/2022 | Jakus |

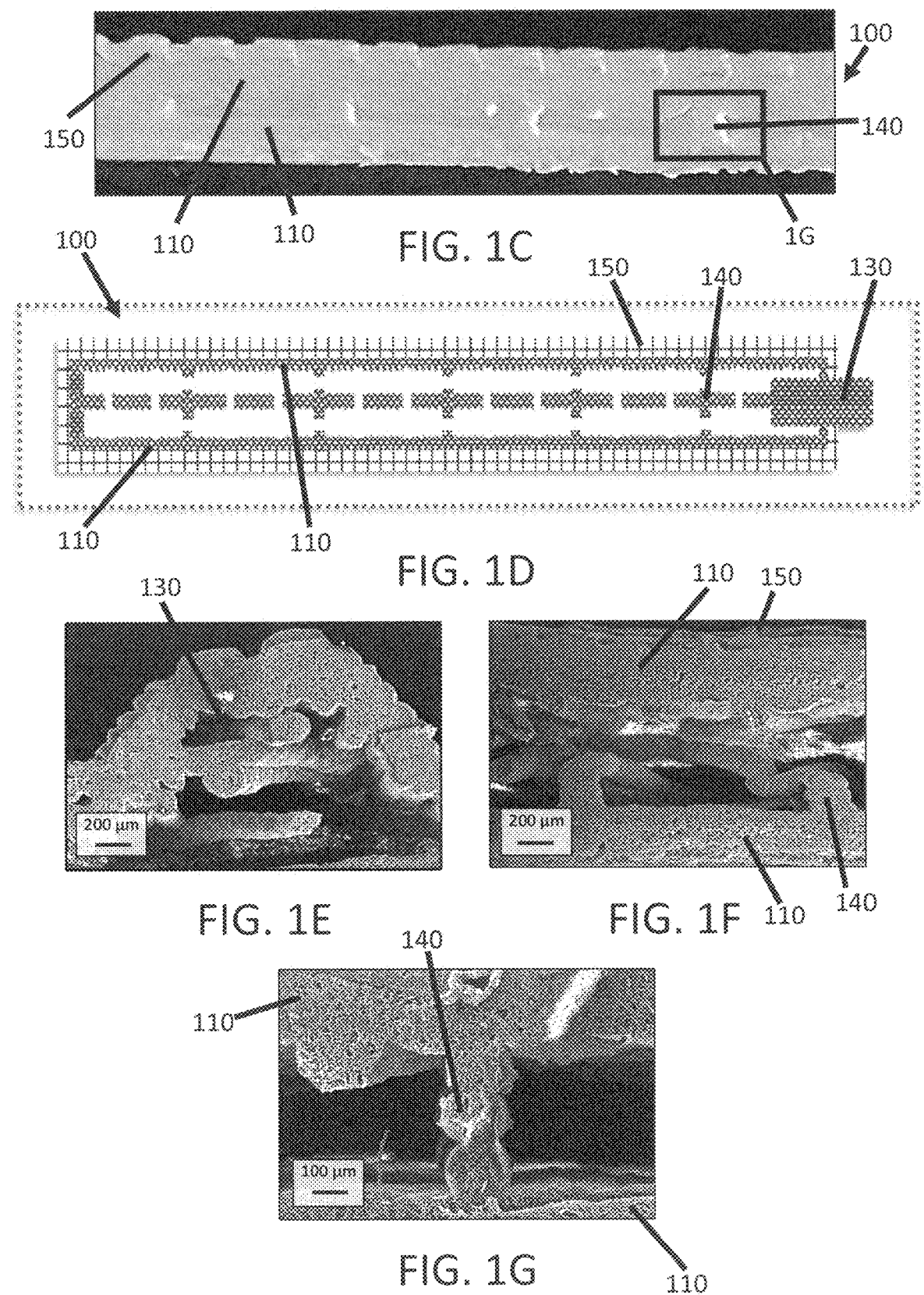

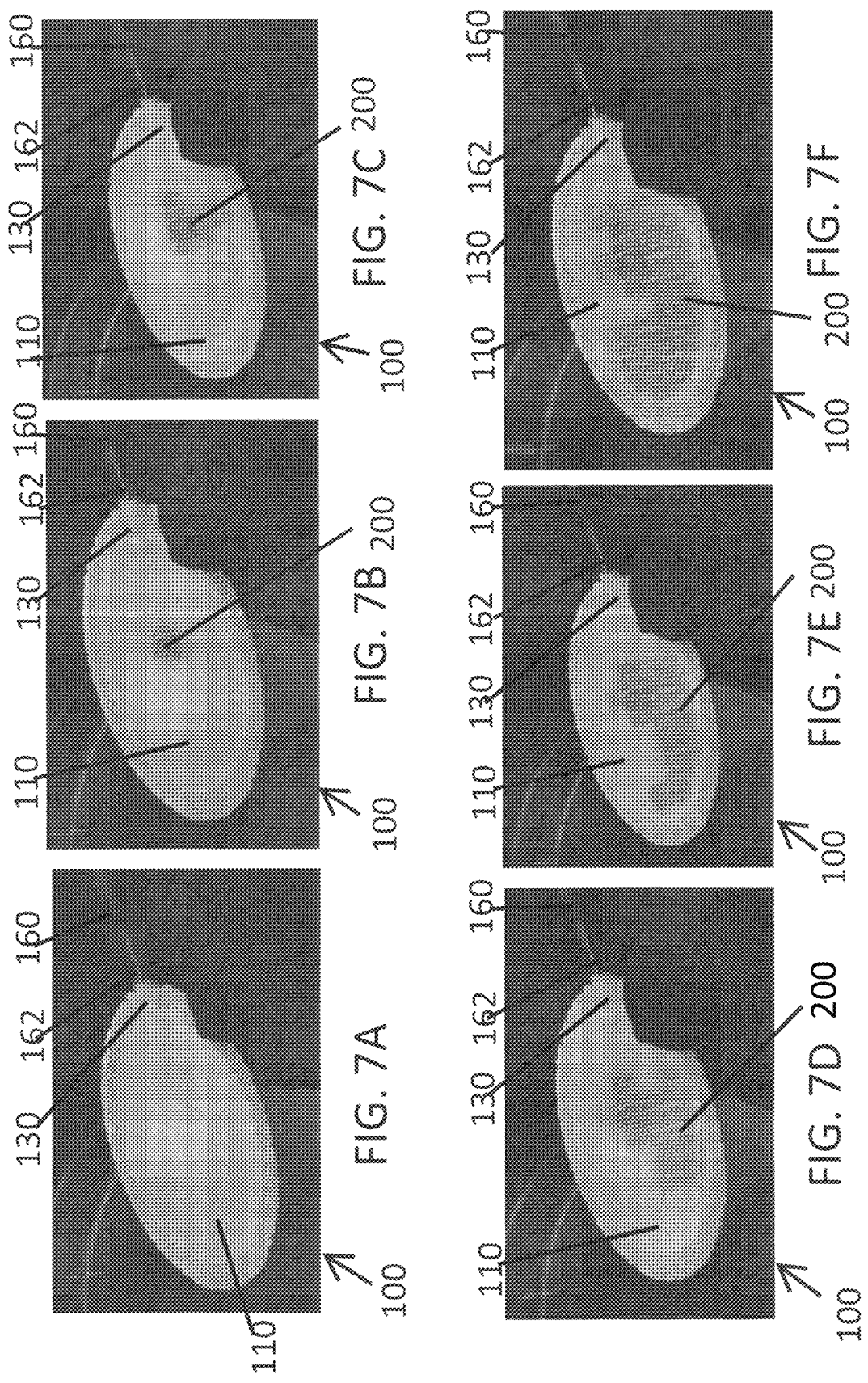

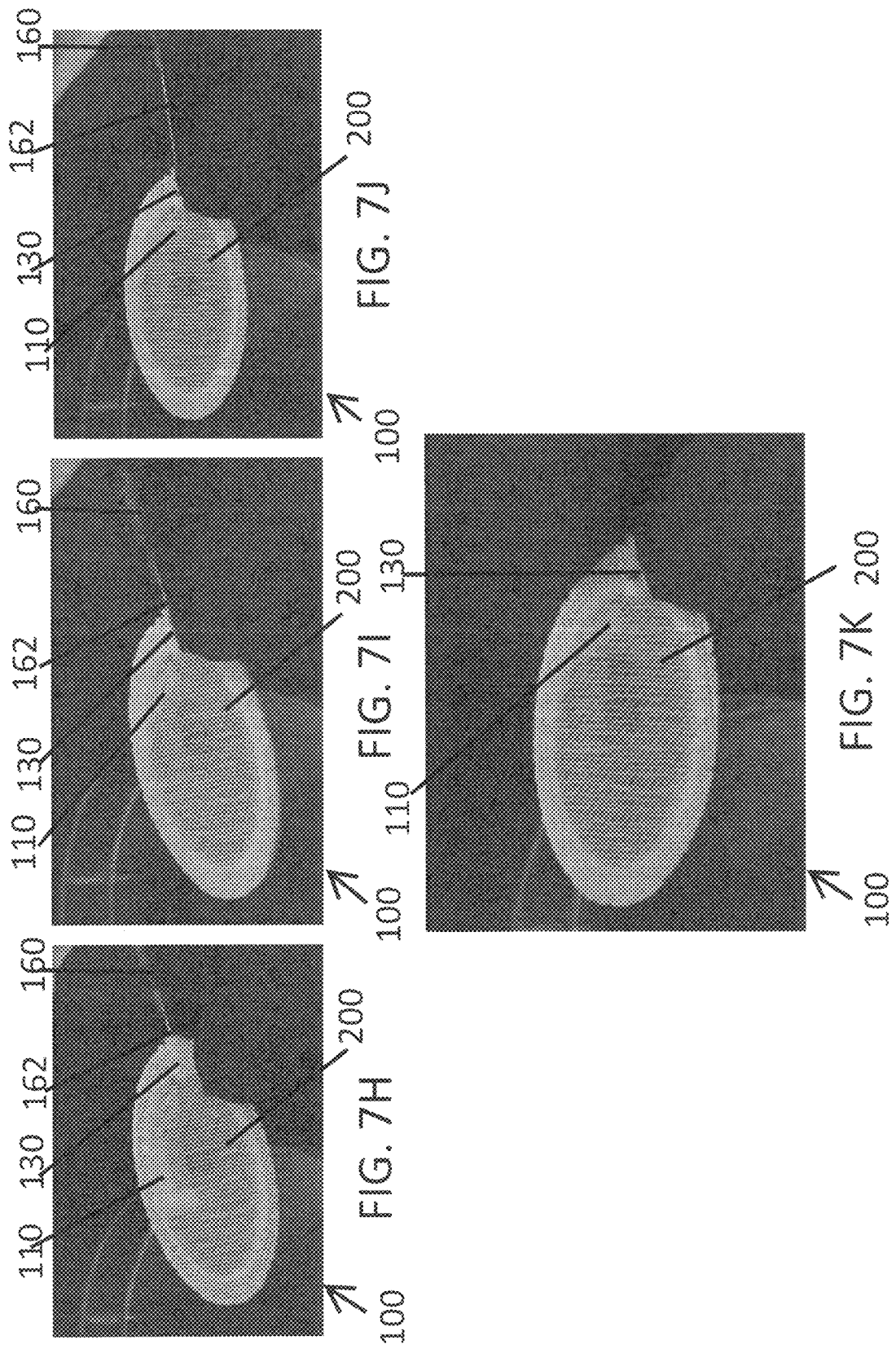

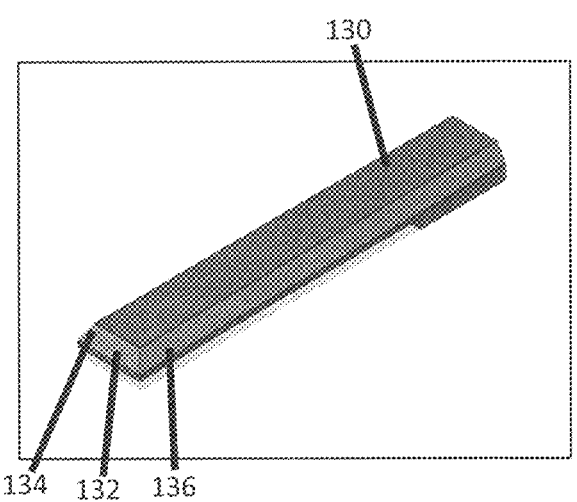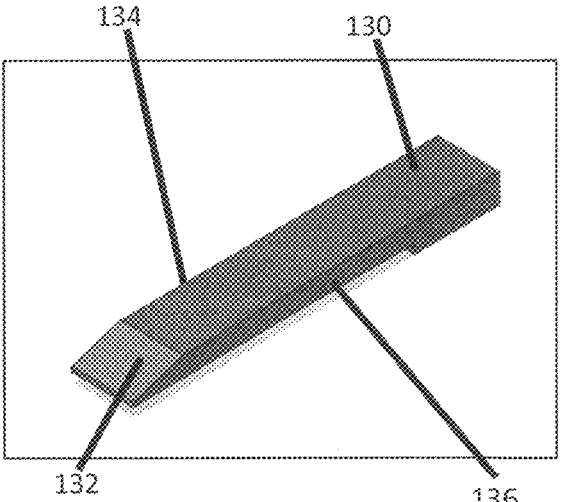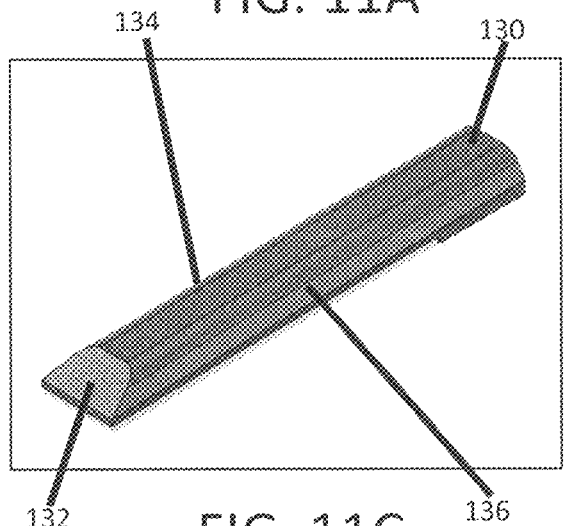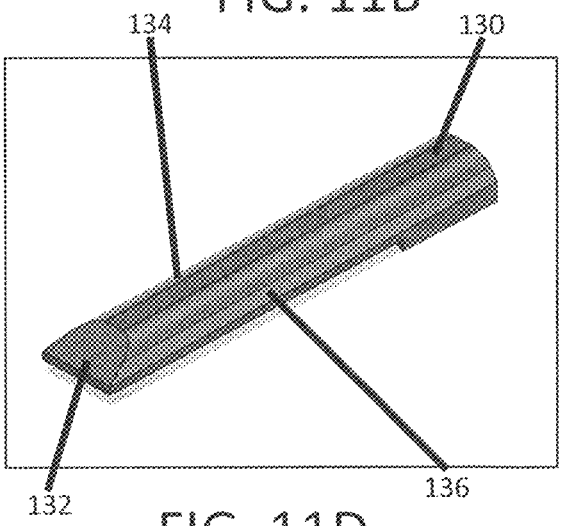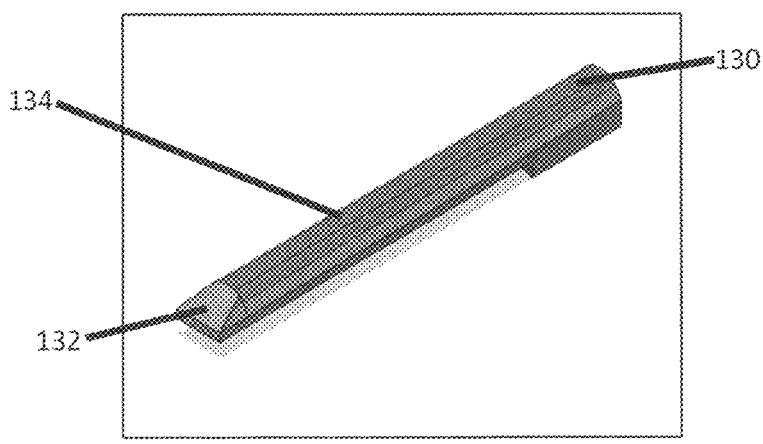

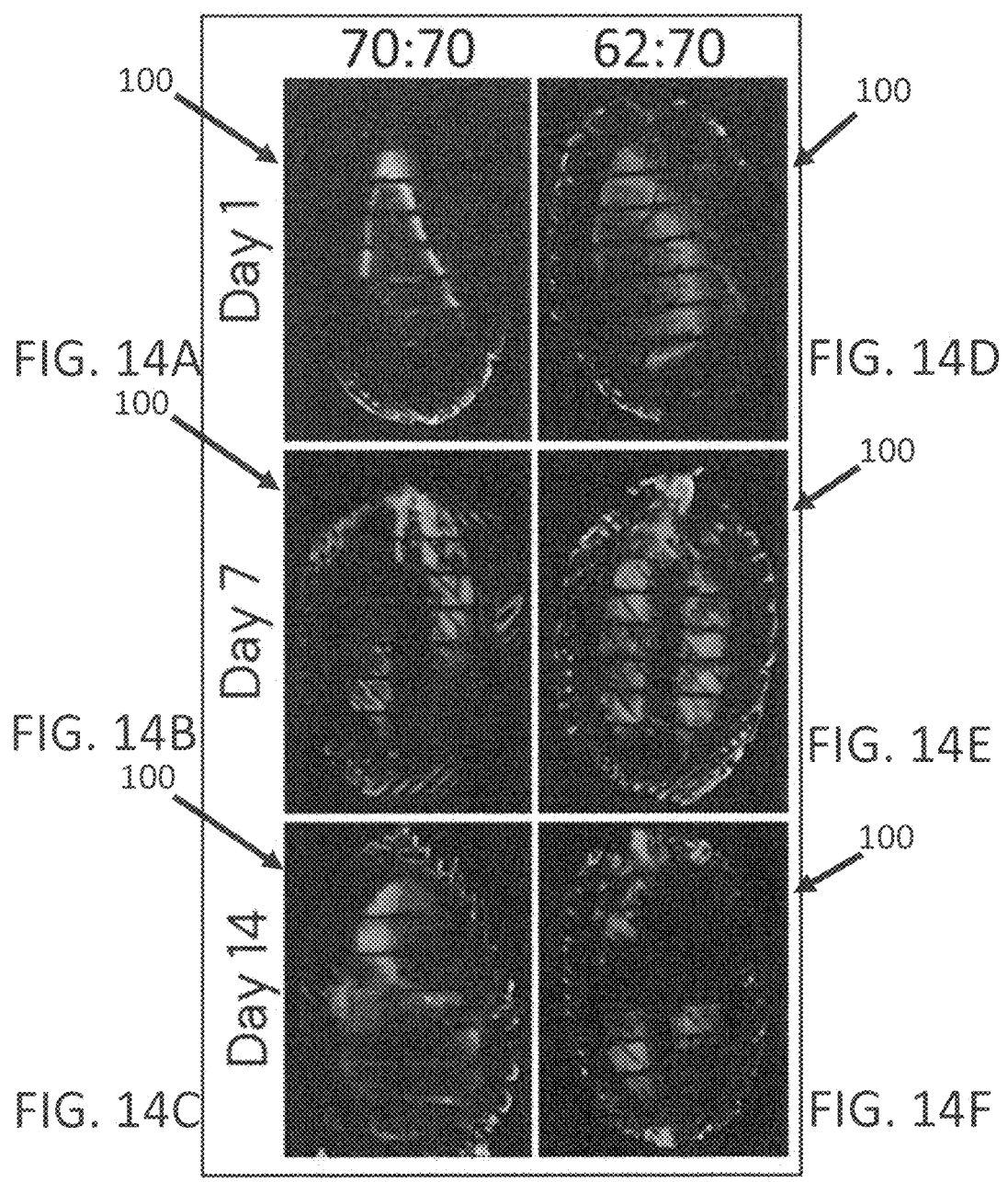

BIOINTEGRATIVE IMPLANTABLE CELL ENCAPSULATION DEVICE AND SYSTEM

CROSS-REFERENCE TO RELATED APPLICATION

This patent application claims priority to and benefit of U.S. Provisional Application No. 63/399,449, filed Aug. 19, 2022, the entire content of this application is incorporated herein by reference.

BACKGROUND

This disclosure relates to implantable devices and, specifically, biointegrative implantable cell encapsulation devices and systems.

Pharmacological interventions have historically relied on biochemical/factor (drug, protein, hormone, etc.) ingestion, injection, topical application, or slow-release, pre-loaded implants. Depending on the pathology being treated, each of these methods have their limitations with respect to factor delivery and its efficiency, efficacy, and safety. Additionally, synthetic synthesis/manufacturing methods do not yet exist or are not yet commercially viable for many biochemistries and other factors that could otherwise be very beneficial in treating a variety of acute and chronic, local or systemic conditions. To address these deficiencies, significant effort has been put into developing cell engineering and cellular manufacturing (i.e., using natural or engineered living cells to manufacture the factor(s) of interest) technologies that are capable of producing and releasing the factor(s) of interest to treat the particular pathology. To effectively utilize this approach the cells must be transplanted into the patient or subject (host); however, the introduction of foreign cells into the body can elicit severe, and even fatal, immunological responses.

In an attempt to overcome this immunological rejection challenge, two categories of approaches have been introduced (used independently or in combination). The first is to utilize immunosuppressants along with the cell transplant. The second is to encapsulate or contain the cells within a gel-based or non-gel-based device or multiple devices prior to or after their implantation into the host. The primary drawbacks of relying on immunosuppressant drugs are increased risk of patient infection, autoimmune responses, as well as a myriad of other negative side effects that can severely impact quality of life or even lead to death. The cell encapsulation and resulting cell-plus-device implantation concept was introduced to eliminate or reduce the need for immunosuppressants as part of the cell therapy. However, current cell encapsulation and implantation approaches still suffer from numerous functional drawbacks, which can include: 1) negative immunological response to the device containing the cells, 2) inadequate immunoisolation of the encapsulated cells, 3) inadequate nutrient, waste, therapeutic or instigative molecule diffusion between the encapsulated cells and the native host tissues, and 4) discomfort to the patient.

Like any device implant, the body's native tissues and comprising cells will respond to the encapsulating device's composition, microstructure, and overall form factor. Depending on the specific nature of the device, the body's response can be advantageous, resulting in vascularization, integration, and new healthy tissue formation within and around the device; or the response can be disadvantageous, resulting in a local, fibrotic immune response, deposition of scar tissue, and biological encapsulation of the device. Thus, the fibrotic and tissue encapsulation responses, in addition to being very uncomfortable and possibly dangerous for the patient, have the added drawback of limiting the effectiveness of the encapsulated cells over time, as the native tissues surrounded the device are typically avascular, effectively choking off the transplanted cells from the nutrients required to survive, and closing off the factor transport mechanisms (vasculature) to the rest of the body. Additionally, current encapsulation devices are mechanically stiff/rigid (less compliant than surrounding tissues), resulting in significant short-term and long-term irritation after implantation. These responses primarily result from the use of traditional implantable polymers and gels in the encapsulation device design.

Beyond these technical and use challenges, the devices that are currently being used in this space are challenging and inefficient to manufacture, requiring the integration of numerous functional components, each individually fabricated using a variety of processes (electrospinning, thermal lamination, micro-injection molding, etc.), and then physically assembled; an approach that limits the form-factor complexity of the device, limits the types of material compositions that can be used to fabricate the device, and increases the risk of introducing catastrophic device defects.

SUMMARY

The current invention addresses the drawbacks of using immunosuppressants as well as current encapsulation device materials and designs. "Materials" as used herein includes both composition and microstructure.

The cell encapsulation system (CES) of the present disclosure is a system and device intended for dermal, subdermal, muscle, tissue, or organ implantation into an individual (host) that is capable of being loading with (e.g., via injection) and carrying and containing exogenously introduced cells (i.e., encapsulated cells) that can produce relevant biochemicals (i.e., factors) that can be transported to the host tissue while simultaneously not eliciting a significant host immune response (i.e., to the implanted device or to the encapsulated cells). A primary intended use of the inventive CES device is to provide a means of local and/or systemic, prolonged delivery of single or multiple therapeutic molecules or factors to alleviate, treat, or cure a variety of acute and chronic pathologies and ailments.

In one embodiment, the CES device comprises recently developed biomaterials, originally designed for tissue repair and regeneration, that promote healthy tissue integration (mitigating or completely eliminating tissue encapsulation upon implantation), while simultaneously immunologically isolating encapsulated cells and allowing their manufactured factors to reach the surrounding host tissue.

Embodiments directed to methods of forming the inventive CES device may utilize room-temperature based extrusion 3D-printing that allows for multi-component, complex devices to be manufactured in a single forming step without requiring assembly. The components may include, injection ports, cell encapsulation chambers, encapsulating membranes, exterior pro-integrative/vascular scaffold textures. Examples of room-temperature based extrusion 3D-printing are found in U.S. Pat. No. 10,584,254 entitled INK COMPOSITIONS FOR THREE-DIMENSIONAL PRINTING AND METHODS OF FORMING OBJECTS USING THE INK COMPOSITIONS, filed 14 Nov. 2016, which is herein incorporated by reference in its entirety (hereinafter referred to as the "'254 patent"). The '254 patent sets forth a (laminarly extrudable, at room-temperature, without chemical or thermal reaction) 3D-printable "ink" created from a series of solvents, biocompatible polymer, and particles/powders. This "ink" can be 3D-printed into a variety of form factors and is also amenable to other manufacturing methods (such as, for example, fiber forming, textiles, weaving, casting, etc.). Additionally, or alternatively, 3D-printing materials and processes of U.S. Pat. No. 9,327,448 entitled METHODS FOR FABRICATING THREE-DIMENSIONAL METALLIC OBJECTS VIA ADDITIVE MANUFACTURING USING METAL OXIDE PASTES, filed 1 Aug. 2014; U.S. Pat. No. 10,236,528 entitled THREE DIMENSIONAL EXTRUSION PRINTED ELECTROCHEMICAL DEVICES, filed 18 Jul. 2016; U.S. Pat. No. 10,350,329 entitled GRAPHENE-BASED INK COMPOSITIONS FOR THREE-DIMENSIONAL PRINTING APPLICATIONS, filed 15 Oct. 2015; U.S. Pat. No. 10,793,733 entitled INK COMPOSITIONS FOR FABRICATING OBJECTS FROM REGOLITHS AND METHODS OF FORMING THE OBJECTS, filed 7 Apr. 2016; U.S. Patent Publication No. 2019/0343989 A1 entitled SURGICALLY-FRIENDLY TISSUE PAPERS FROM ORGAN-SPECIFIC DECELLULARIZED EXTRACELLULAR MATRICES, filed 16 May 2019; and U.S. Patent Publication No. 2020/0353129 A1 entitled WATER-SOLUBLE SALT PARTICLE CONTAINING COMPOSITIONS AND POROUS MATERIALS MADE THEREFROM, filed 29 Apr. 2020; U.S. Pat. No. 11,654,214 entitled CERAMIC-CONTAINING BIOACTIVE INKS AND PRINTING METHODS FOR TISSUE ENGINEERING APPLICATIONS, filed 26 Apr. 2018; and U.S. Patent Publication No. 2022/0401630 A1 entitled METHOD FOR FABRICATION OF ADDITIVELY MANUFACTURED, SELF-GELLING STRUCTURES AND THEIR USE, filed 18 Mar. 2022 may be used with or to support the present invention, all of which are herein incorporated by reference in their entirety.

The inventive materials and fabrication methods are leveraged to create implantable cell encapsulation devices with one or more of the following characteristics:

(a) Material composition in combination with material microstructure allows it to be punctured by a syringe needle, enabling ready loading of cells, while being easy to seal off (mechanical pinching, cutting, or pressing, with or without thermal aid;

(b) Single loading can be used to fill multiple cell chambers within the device (with singular or multiple cell types);

(c) The material comprising the encapsulating membrane component of the system is porous with nanometer to micron sized pores ("nano-to-micron porous"), allowing for nutrient, waste, and target factor diffusion, while preventing traversal of contained cells into the surrounding host tissue and traversal of host tissue cells into the encapsulating cell chambers, inhibiting direct interaction of encapsulated cells with the host tissue;

(d) The inherent nano-micron porosity of the comprising materials allows for rapid wicking/absorption of surrounding physiological fluids and their components, while preventing native cell infiltration into the cell encapsulation chambers;

(e) The exterior of the CES devices is comprised of and/or supports biomaterials that promote healthy tissue integration and vascularization, particularly vascularization to the exterior surface of the cell encapsulating membrane, which increases efficacy and efficiency of encapsulated cell manufactured factors and promotes encapsulated cell health and longevity;

(f) The CES devices are comprised of materials that, once hydrated, have a similar mechanical compliance to the surrounding tissue, which mitigates short-term and long-term irritation and discomfort.

(g) The device, regardless of its size, or compositional or architectural complexity (number of ports, encapsulation chambers, etc.) is fabricated in a single forming (3D-printing) step, rather than requiring numerous distinct manufacturing steps, followed by joining individually manufactured components to provide a mechanical platform with varying combinations of components (e.g., lobe(s), injection port(s), encapsulation chamber(s), encapsulating membrane(s), support structure(s), pro-integration/vasculature texture(s), port-tubing connector(s), suture anchor point(s), integrated electrode(s), combinations thereof, etc.) and that may be relied on in a variety of combinations, the importance of each described in greater detail, individually and in exemplary combinations, herein; and (h) If desired, the material(s) comprising the CES device can be pre-embedded with therapeutic molecules, biochemical factors, drugs, etc. to promote initial vascularization, cell survival, biological targeting, etc.

In examples, a cell encapsulation system of the present disclosure comprises a 3D-printed tissue-integrative scaffold and a cell containment bladder, which comprises open cell encapsulation chambers surrounded by or formed by materially porous, but structurally solid, 3D-printed encapsulation membrane(s) (referred herein as "cell encapsulation membrane(s)). In other words, the cell encapsulation bladder comprises the cell encapsulation chamber(s) and the surrounding cell encapsulation membrane or cell encapsulation chamber(s) formed by the cell encapsulation membrane. While the 3D-printed scaffold may comprise a material, or be made from a material, having a material porosity, the 3D-printed scaffold may additionally comprise scaffold pores, referred herein as structural porosity, formed from said material. As used herein, structural porosity is defined as physically open space between deposited, or otherwise placed, materially porous features (e.g., fibers). In other words, structural porosity is the physical spacing formed between adjacently deposited fibers that are separated from one another. Comparatively, as used herein, material porosity is defined as porosity of the material itself and is a material property, and not the porosity formed by the stacking of layers of the material (e.g., fibers). Material porosity may be of a nano-to-micron scale while structural porosity of the scaffold may be from tens of microns to thousands of microns, or greater.

The 3D-printed scaffold may be of a material composition comprising biomaterials. The 3D-printed bladder, comprising the cell encapsulation membrane(s) and encapsulation chamber(s), may be formed within the 3D-printed scaffold where the 3D-printed bladder is relied on for encapsulating cells. In examples, the 3D-printed printed bladder, or any encapsulation chamber(s) formed therein, contains the cells, encapsulating the cells within the bladder or chamber, whose boundaries are defined by the materially porous solid encapsulating membranes. The cells encapsulated within the cell encapsulation bladder or chamber(s) therein may be accompanied by a fluid. The 3D-printed scaffold and/or 3D-printed cell encapsulation membrane (and, thereby, the cell encapsulation bladder or chamber(s)) may comprise multiple architectures in a single contiguous device. 3D-printed scaffold is formed through room-temperature based extrusion 3D-printing. In examples, the 3D-printed scaffold and the materially porous solid 3D-printed cell encapsulation membrane, and thereby the corresponding bladder and/or any chamber(s) formed therefrom, are each formed through room-temperature based extrusion 3D-printing. In examples, the 3D-printed scaffold and the materially porous solid 3D-printed cell encapsulation membrane are a single room-temperature based 3D-printed object formed through the same room-temperature based extrusion 3D-printing. In examples, the 3D-printed scaffold and the 3D-printed cell encapsulation membrane may be embedded with one another. In examples, the 3D-printed scaffold and/or the materially porous solid 3D-printed cell encapsulation membrane may be translucent to visualize the fluids and/or the cells therein or the addition of the fluids and/or the cells therein.

In examples, a material composition of the 3D-printed scaffold or portions thereof may comprise and/or support added biochemical factors, therapeutic molecules, or the like. The material composition may be biodegradable, non-biodegradable, or a combination thereof (e.g., portions thereof may be a combination of biodegradable and non-biodegradable properties). The material composition may comprise and/or support added genetic material (e.g., plasmids, single stranded DNA, double stranded DNA, mRNA, tRNA, rRNA, or the like). The material composition may comprise and/or support added functionalized nano- and microparticles capable of responding to local environmental stimuli. The material composition may comprise and/or support added nano- or micro-machined mechanical, electronic, photonic, or combination thereof. The material composition may comprise and/or support a chemically modified surface. The material composition may comprise and/or support a varying microstructure across the device or components of the device. The material composition may comprise and/or support a combination of the above.

A material composition of the materially porous solid 3D-printed cell encapsulation membrane or portions thereof (e.g., such as that relied on to form the port, port components, bladder, chamber, chamber components, etc.) may comprise and/or support added biochemical factors, therapeutic molecules, or the like. The material composition may be biodegradable, non-biodegradable, or a combination thereof (e.g., portions thereof may be a combination of biodegradable and non-biodegradable). The material composition may comprise and/or support added genetic material (e.g., plasmids, single stranded DNA, double stranded DNA, mRNA, tRNA, rRNA, or the like). The material composition may comprise and/or support added functionalized nano- and microparticles capable of responding to local environmental stimuli. The material composition may comprise and/or support added nano- or micro-machined mechanical, electronic, photonic, or combination thereof. The material composition may comprise and/or support a chemically modified surface. The material composition may comprise and/or support a varying microstructure across the device or components of the device. The material composition may comprise and/or support a combination of the above.

Any combination of the material composition of the 3D-printed scaffold or portions thereof and material composition of the materially porous solid 3D-printed cell encapsulation membrane or portions thereof may be any combination of features noted herein. A material composition of one or more of the 3D-printed scaffolds, the materially porous solid 3D-printed cell encapsulation membrane, combinations thereof, or portions thereof may further comprise and/or support biochemical factors. Biochemical factors may comprise one or more of hormones, growth factors, cytokines, peptides, proteins, proteoglycans, enzymes, proteinases, antibiotics, antivirals, antifungals, polysaccharides, opioids, small molecule drugs, and exosomes. In examples, the materially porous solid membrane component(s) of the 3D-printed bladder and/or chamber(s) therein is a nano-micron porous allowing for nutrient, waste and target form factor diffusion while preventing direct interaction of the encapsulated cells with host tissue and the scaffold pores of the 3D-printed scaffold having direct interaction with the host tissue. Hence, it is referred to as a materially porous, but structurally solid (not structurally porous), 3D-printed encapsulation membrane or, in shorter form, a materially porous solid 3D-printed cell encapsulation membrane.

In examples, the 3D-printed fibers of the 3D-printed scaffold are stacked in arrangements with spaces therebetween form the scaffold pores (i.e., structural porosity) of the 3D-printed scaffold or the 3D-printed fibers are stacked in arrangement with no spacing therebetween, such that no structural pores (i.e., structural porosity) are formed forming the materially porous solid 3D-printed cell encapsulation membrane. In arrangements, the 3D-printed fibers of the 3D-printed scaffold and/or the 3D-printed fibers of the 3D-printed cell encapsulation membrane may comprise complex configurations, such as each fiber within a given layer may be defined by a: sine wave, saw tooth wave, honeycomb, geometric space-filling pattern, a combination thereof, or the like. In examples, the materially porous solid 3D-printed cell encapsulation membrane may be fully enclosed within the 3D-printed scaffold. In examples, the materially porous solid 3D-printed cell encapsulation membrane may be partially enclosed within the 3D-printed scaffold.

Formation of the 3D-printed fibers of the 3D-printed scaffold and the 3D-printed fibers of the cell encapsulation membrane may be done through material extrusion additive manufacturing. The additive manufacturing may be done through in-plane extrusion processes (3-axis). The additive manufacturing may be done through out-of-plane extrusion processes (>3-axis). All or portions of the 3D-printed fibers of the 3D-printed scaffold and/or all or portions of the 3D-printed fibers of the cell encapsulation membrane may be formed through planar or volumetric stereolithographic, direct light projection, or other forms of additive manufacturing. Further the device, or portions thereof, may be formed by 3D-printing on top of or around an existing two-dimensional or three-dimensional template. The template may be coated with a material to which the 3D-printed material adheres. The template may be physically removed or dissolved away from the structure after 3D-printing and post-processing is complete. The material coating of the template may be different from the material(s) 3D-printed onto or around the template. Prior to storage or use, but after initial fabrication, the device may undergo additional forming steps, including but not limited to bending, folding, rolling cutting, etc. The device may also undergo physical surface modifications during or after initial fabrication, including but not limited to surface roughening, surface smoothing, laser hole drilling/cutting, etc. Additionally, or alternatively, the CES device may be formed by a non-3D-printing process, including but not limited to dip-coating a pre-existing form, electrospinning, spin-casting, casting, etc. Additive manufacturing further provides the flexibility of stopping and restarting the printing process for incorporation of components or layers formed by alternative manners of construction or formation. Coatings may also be applied to components of the present 3D-printed structures in a similar manner.

In examples, the 3D-printed scaffold and/or the 3D-printed cell encapsulation membrane (e.g., port, port components, bladder, chamber, chamber components, etc. formed thereby) may be hydrated by fluids after formation, with the loading of cells, and/or after implantation within a host. In examples, one or more of the 3D-printed scaffolds, the materially porous solid 3D-printed cell encapsulation membrane, a combination thereof, or portions thereof (e.g., port, port components, chamber, chamber components, etc.) are biodegradable. In examples, one or more of the 3D-printed scaffold, the materially porous solid 3D-printed cell encapsulation membrane, a combination thereof, or portions thereof (e.g., port, port components, chamber, chamber components, etc.) are non-biodegradable.

In examples, the CES device comprises a port for inserting cells into the bladder and/or chambers formed by the materially porous solid 3D-printed cell encapsulation membrane. The 3D-printed bladder and/or chambers may comprise internal porous supports perpendicular or oblique to the port and extending across the port. The 3D-printed bladder and/or chambers may comprise internal porous supports parallel to the port. In examples, the 3D-printed bladder may comprise a single chamber. In examples, the 3D-printed bladder may comprise a plurality of chambers divided by chamber walls wherein each chamber is accessible through the port. The chamber walls may be perpendicular or oblique to the port. In examples, the port may be self-sealing. In examples, the port may be sealed by heating or local melting. In examples, the port may extend from the 3D-printed scaffold. In examples the port may comprise port walls and an internal channel having a greater porosity than the port walls for guiding a needle through one or more chambers.

A method of forming the cell encapsulation system or device of the examples above may comprise the steps of: (a) 3D-printing fibers in an alternating arrangement to form the 3D-printed scaffold with the scaffold pores therein; and (b) changing a direction of the fibers to 3D-print the fibers in a side-by-side or in-line arrangement with no spacing therebetween to form the materially porous solid 3D-printed cell encapsulation membrane. The method may further comprise a single forming step for forming the 3D-printed scaffold, the materially porous solid 3D-printed cell encapsulation member, and/or the corresponding 3D-printed bladder and/or chambers with numerous architectures. The forming step may be by additive manufacturing, such as the additive manufacturing examples for formation identified above.

A method of loading a cell encapsulation system or device of the examples herein may comprise the steps of: (a) inserting a loading device (e.g., syringe, syringe needle, flexible tubing, pump, automated system, a combination thereof, or the like) into one or more injection ports of the device; (b) loading a fluid and cells into the 3D-printed bladder and/or one or more of the chambers formed therein from the loading device, wherein the materially porous solid 3D-printed cell encapsulation membrane of the bladder and/or chambers allows diffusion of the fluid into and out of the cell encapsulation bladder and/or chambers while cells are maintained within the cell encapsulation bladder and/or chambers; (c) removing the loading device from the bladder and/or one or more chambers as the bladder and/or the one or more chambers fill; (d) removing the loading device from the injection port; (e) sealing the injection port to maintain the cells therein. In the method of operating and the step of inserting the loading device the loading device may be inserted into a port of the CES device, or component thereof, the port having a different architecture than the bladder and/or the one or more chambers thereof and the one or more porous supports within the 3D-printed bladder and/or the one or more chambers wherein the loading device is guided by the port and punctures the one or more porous supports within the 3D-printed bladder and/or the one or more chambers to reach additional chambers of the one or more chambers. In the step of sealing the port in the method of loading the port may be pinched to maintain the cells therein. In examples, the port may be additionally, or alternatively, heated or locally melted to maintain the cells therein.

A method of implanting a cell encapsulation system or device of the examples herein may comprise the steps of (a) implanting one or more cell encapsulation systems or devices with dermal, sub-dermal, muscle, cartilage, osteochondral, fatty, or composite connective tissues thereof in a host; and/or (b) implanting one or more of the cell encapsulation systems or devices on-top of, immediately adjacent to, or within non-connective tissues and organs. The non-connective tissues and organs may comprise one or more of cardiac, kidney, liver, ovarian, testicular, brain, spinal cord, vascular, endocrine, ocular, or other composite tissue in the host. The steps of implanting may further comprise being physically implanted and placed by forceps after a step of tissue incision of the host. Alternatively, the steps of implanting may include the implant being placed non-invasively using annular, endoscopic and other minimally invasive surgical techniques. In examples, the device may comprise structurally auxetic regions that may be collapsed to assist minimally invasive deployment. The auxetic regions may then return to original form or structure after deployment. The method of implanting may further comprise a step of (c) retaining the one or more cell encapsulation systems or devices within the host after termination of a treatment such that there is no removal of the one or more cell encapsulation systems from the host after implanting. In examples, the cells and other device contents may be removed without the need for device explantation via syringe extraction. Alternatively, the method of implanting may further comprise a step of (d) explanting the one or more cell encapsulation systems or devices from the host to ex vivo tissues and/or organs contained within a culture and/or a bioreactor system. In examples, the implanted device may be retrieved or explanted before, during, or after integration with surrounding tissue, via surgical explantation. In examples, the one or more cell encapsulation systems or devices may further comprise suture anchors. The one or more cell encapsulation systems or devices may be mechanically affixed to surrounding tissue of a host and/or to separate device(s) via the suture anchors. Additionally, or alternatively, the one or more cell encapsulation systems or devices may be affixed to surrounding tissue via adhesive glue. In addition to the steps above, the method of implanting the one or more cell encapsulation systems or devices may comprise one or more steps of positioning and/or orientating the device after implantation.

In examples, the method of implanting may further comprise a step of (e) loading the one or more of the cell encapsulation systems or devices with cells prior to the steps of implanting. Additionally, or alternatively, the method of implanting may further comprise a step of (f) loading the one or more cell encapsulation systems or devices with cells after the steps of implanting. In some examples, the cells loaded prior to the steps of implanting may be the same as the cells loaded after the steps of implanting. In some examples, the cells loaded prior to the steps of implanting may be different than the cells loaded after the steps of implanting.

A method of utilizing a cell encapsulation system or device may comprise a step of applying one or more of the cell encapsulation systems or devices to ex vivo tissues and/or organs contained within a culture and/or a bioreactor system. In some examples, the ex vivo tissues and/or organs may be explanted. In some examples, the ex vivo tissues and/or organs are engineered.

A method of operating the cell encapsulation system or device is also contemplated. A method of operating the cell encapsulation system or device may comprise steps of: (a) rapidly vascularizing and integrating the 3D-printed scaffold with surrounding tissue of a host after a step of implanting the cell encapsulation system or device into the host; (b) preventing native tissue and vasculature from coming into direct contact with encapsulated cells within the 3D-printed bladder and/or one or more chambers through the materially porous solid 3D-printed cell encapsulation membrane; (c) preventing the encapsulated cells within the 3D-printed bladder and/or the one or more chambers from escaping or migrating from the 3D-printed bladder and/or the one or more chambers; (d) maintaining viability of the encapsulated cells through nutrient and waste diffusion through the materially porous solid 3D-printed cell encapsulation membrane; and diffusing biomolecular products produced by the encapsulated cells through the materially porous solid 3D-printed cell encapsulation membrane into the host via vasculature. The method of operating may further comprise (f) self-regulating biomolecular production by controlling production of target factors of the encapsulated cells based on signaling molecules in the host. In one example, the encapsulated cells may be induced to increase production of the target factors based on the signaling molecules in the host. Additionally, or alternatively, the encapsulated cells may decrease production of the target factors based on the signaling molecules in the host.

Also contemplated herein are methods of treating various ailments and conditions by using the CES device to deliver a therapeutically effective amount of one or more types of cells or other biomolecular products to a patient in need of such a treatment. For example, a method of treating ailments and conditions using the CES device described herein comprises a step of: delivering a therapeutically effective amount of one or more types of cells or other biological factors in the cell encapsulation system to a host in need of such treatment.

Also contemplated herein are methods of integrating the CES device with other separate components. By example, the CES device may be physically integrated with independently manufactured membranes(s), sensor(s), biosensor(s), electronic(s), microelectronic(s), fluidic(s), microfluidic(s), or other electrical, mechanical, electromechanical, photonic, or piezo device(s) prior to use. The CES device may comprise an electrode connected with external electrical systems. In examples, the device may additionally, or alternatively, be integrated with independently manufactured communication devices, including but not limited to those that transmit data or information (e.g., radio frequencies, Bluetooth® Technology frequencies, etc.). The above-mentioned components may be physically integrated into the CES device during the cell encapsulation device's fabrication (i.e., manually or robotically placed after a respective layer is printed, and, thereafter, continue printing on top of the separate component).

The foregoing and other objects, features, and advantages of the examples will be apparent from the following more detailed descriptions of particular examples as illustrated in the accompanying drawings wherein like reference numbers represent like parts of the examples.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Reference is made to the accompanying drawings in which particular examples and further benefits of the examples are illustrated as described in more detail in the description below, in which:

FIG. 1C is a photographic image of a cross-section of a Cell Encapsulation System (CES) device taken at line 1C-1C of FIG. 1, in accordance with an example of the disclosure.

FIG. 1D is a digital representation of the photographic image of FIG. 1B, in accordance with an example of the disclosure.

FIG. 1E is a sectional view of the photographic image of FIG. 1A taken at section 1E, in accordance with an example of the disclosure.

FIG. 1F is a sectional view of the photographic image of FIG. 1B taken at section 1F, in accordance with an example of the disclosure.

FIG. 1G is a sectional view of the photographic image of FIG. 1C taken at section 1G, in accordance with an example of the disclosure.

FIG. 4A illustrates a cross-sectional view of the injection port with side walls open to allow cells to access the chambers of the device, FIG. 4B illustrates the chambers divided by walls of material that can be punctured by a syringe and with a syringe placed through a port and said walls, FIG. 4C illustrates cells loading from the back of the device forwards, and FIG. 4D illustrates the syringe extracted and an end of the port mechanically and/or thermally pinched to seal cells within the CES device, each in accordance with an example of the disclosure.

FIG. 5A illustrates a CES device as manufactured, FIG. 5B illustrates a needle puncturing the CES device and inserted through an injection port and multiple chambers in order to fill the CES device with fluid and/or cells, FIG. 5C illustrates the CES device after removal of the needle and after having been filled by fluid and/or cells such that the port may be further pinched, with or without heat, to seal the fluid and/or cells within the CES device, and FIG. 5D illustrates the CES device having been filled by fluid and/or cells and ready for use, each in accordance with an example of the disclosure.

FIG. 6A is a top view of the materially porous solid cell encapsulation membrane printed therein with side walls and for containing cells with a base of a cell encapsulation membrane and an injection port being formed. FIGS. 6B-6D are further progressive top views of the 3D-printing process forming the exterior scaffold layer, cell encapsulation membrane, and port, each in accordance with an example of the disclosure.

FIGS. 7A-7F and 7H-7K are progressive images of a representative example of a Cell Encapsulation System (CES) device with fluid and/or cells being loaded therein by a syringe, where in FIG. 7A the syringe is inserted through an injection port into the device. FIGS. 7B-7F and 7H-7J progressively illustrate the fluid and/or cells being loaded therein. FIG. 7K illustrate the syringe removed and the injection port being pinched to seal the fluid and/or cells within the device, each in accordance with an example of the disclosure.

FIGS. 11A-11E are digital representations of top views of examples of injection ports of Cell Encapsulation System (CES) devices, in accordance with examples of the disclosure.

FIG. 12A is of a single-lobe configuration, FIG. 12B is of a four-lobe configuration, FIG. 12C is of a donut configuration, and FIG. 12D is of a tube template configuration, in accordance with examples of the disclosure.

FIGS. 14A-14F are scanning florescent confocal images of cross-sections of Cell Encapsulation System (CES) devices, where FIGS. 14A-14C are images of CES devices formed of a single material with the images taken at one (1) day, seven (7) days, and fourteen (14) days after loading each with nominally 1 million human HUH7 cells, respectively, and FIGS. 14D-14F are images of cross-sections of CES devices formed of two materials with the images taken at one (1) day, seven (7) days, and fourteen (14) days after loading each with nominally 1 million human HUH7 cells, respectively, in accordance with examples of the disclosure.

DETAILED DESCRIPTION

Figure 1:
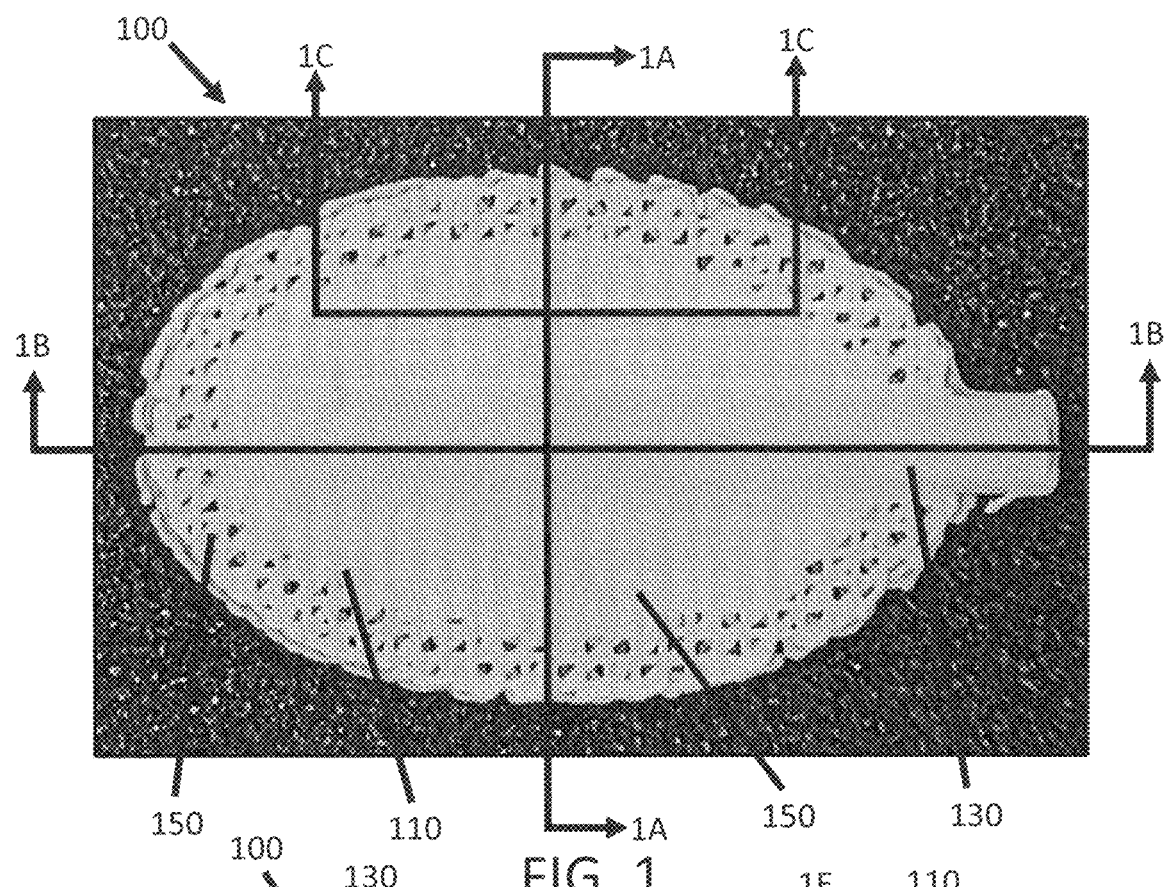
FIG. 1 is a top view of a representative photographic image of a Cell Encapsulation System (CES) device with an injection port extending through the majority of the device length that additionally protrudes from the top to facilitate easier loading into the device, in accordance with an example of the disclosure.

The cell encapsulation system (CES) is a device intended for dermal, subdermal, muscle, tissue, or organ implantation into an individual (host) that is capable of being loading with (e.g., via injection) and carrying and containing exogenously introduced cells (encapsulated cells) that can produce relevant biochemicals (factors) and/or therapeutic molecules that can be transported to the host tissue while simultaneously not eliciting a significant host immune response (to the implanted device or to the encapsulated cells). The intended use of the invention is to provide a means of local and/or systemic, prolonged delivery of single or multiple factors and/or therapeutic molecules to alleviate, treat, or cure a variety of acute and chronic pathologies and ailments.

The CES device allows for facile injection and loading of exogenously introduced cells into predefined, manufactured chambers, which are surrounded by a solid, but nano-to-micron porous membrane. The CES design, in combination with its material compositions, may physically isolate the encapsulated cells from the host immune system, as well as host immune system from the encapsulated cells, while simultaneously allowing biochemical exchange/transport to occur between the host tissue and the encapsulated cells. The CES device is further designed to promote healthy integration of native host tissue and vasculature with the device exterior, mitigating acute and chronic encapsulation/fibrosis and other non-specific immunological response to the implanted device, while further promoting biochemical exchange/transport between the immunologically isolated (i.e., optionally immunoselected), encapsulated cells and the host tissue. These characteristics are made possible, for example, through the use of: 1. Device composition, 2. Device design, or 3. Means of device fabrication/manufacture.

Alternatively, the CES device may be used for non-implant applications, including assisted biomanufacturing and collection of factors and/or therapeutic molecules (i.e., biomanufacturing cells, where the word "cells" is being used here similarly to how it would be used for "manufacturing cell" in manufacturing nomenclature).

FIGS. 1, 1A-1C, and 1E-1G are photographic images of a representative example of a Cell Encapsulation System (CES) device 100. Features, benefits, and advantages of the CES device are described therewith. The device 100 comprises a sub-cell-scale materially porous solid cell encapsulation membrane 110, internal porous supports 140, an injection port 130, and an exterior scaffold 150. FIGS. 1A-1C and 1E-1G are scaled images, measured at the provided representative scale for each. FIG. 1D is a digital representation of the cross-section as illustrated and described by FIG. 1C.

Figure 2:
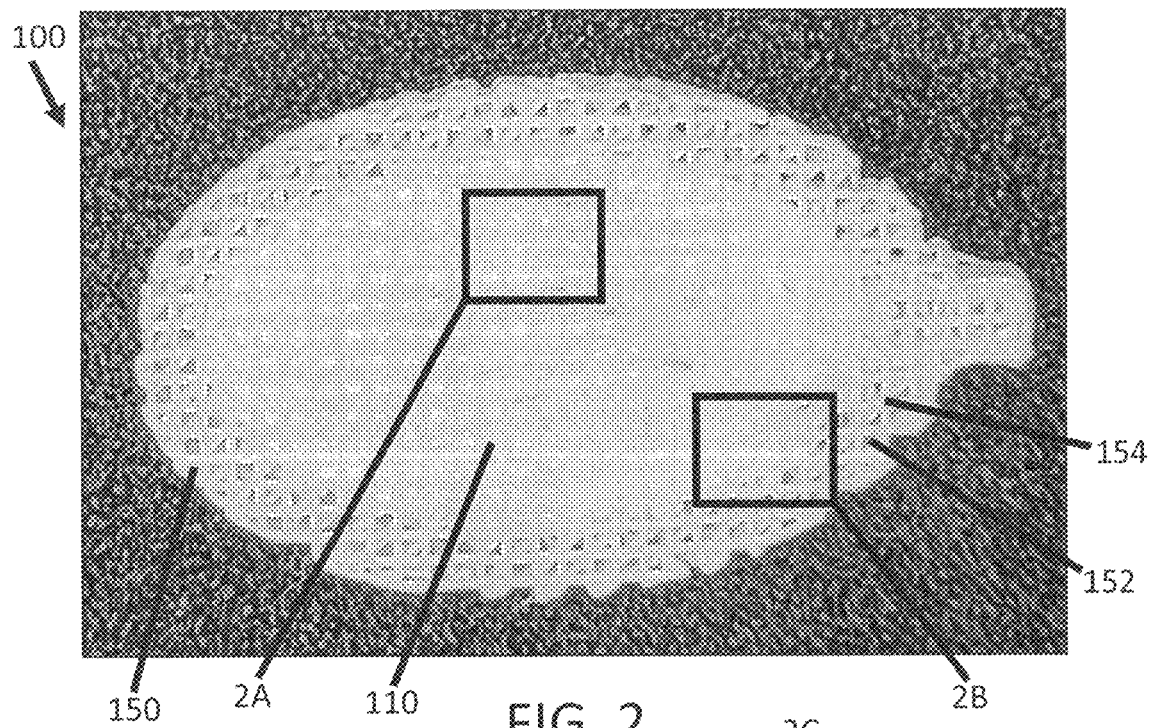
FIG. 2 is bottom view of a representative photographic image of a Cell Encapsulation System (CES) device with exterior scaffold layers that are structurally porous to promote integration with and vascularization by the host tissue, and an interior nano-micron porous membrane that is printed solid to contain cells, in accordance with an example of the disclosure.
Figure 2A:
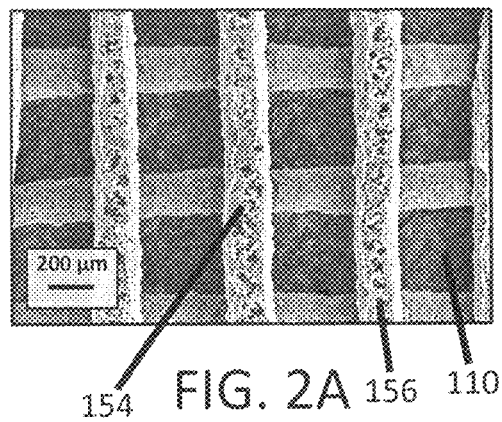
FIG. 2A is a sectional view of the photographic image of FIG. 2 taken at section 2A, in accordance with an example of the disclosure.
Figure 2B:
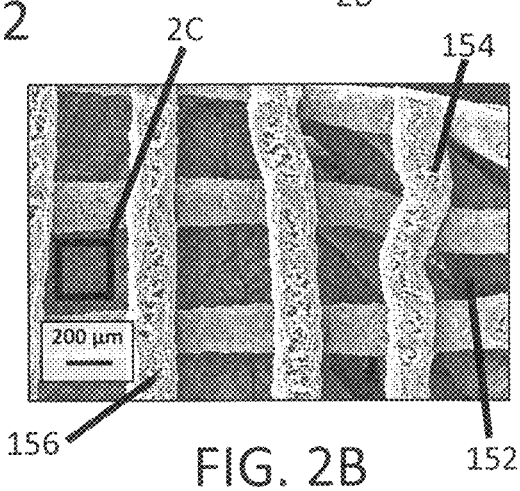
FIG. 2B is a sectional view of the photographic image of FIG. 2 taken at section 2B, in accordance with an example of the disclosure.
Figure 2C:
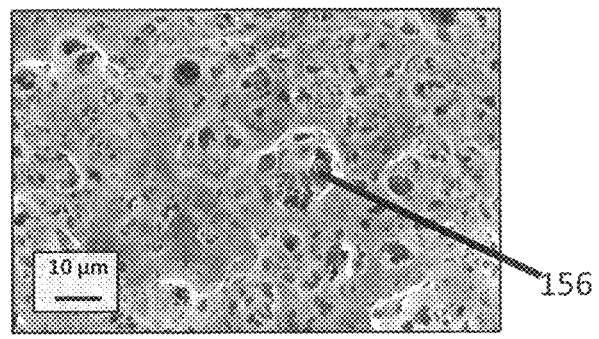
FIG. 2C is a sectional view of the photographic image of FIG. 2B taken at section 2C, in accordance with an example of the disclosure.

FIGS. 2 and 2A-2C are photographic images of a bottom view of a representative example of a Cell Encapsulation System (CES) device 100. FIGS. 2A-2C are scaled images, measured at the provided representative scale for each. The bottom view illustrates the device 100 with an exterior scaffold 150 and a materially porous solid cell encapsulation membrane 110 therein. The exterior scaffold 150 layers are porous to promote integration and vascularization. This may include scaffold porosity and/or material porosity. Scaffold porosity includes pores 152 formed by way of the construction of the scaffold 150 such as, for example, pores 152 formed in the scaffold 150 in a manner of stacking the layers, or fibers 154, of the scaffold 150 at the time of 3D-printing or extrusion (e.g., the voids formed between the stacked components or layers). Alternatively, material porosity includes pores 156 that are in the material properties of the scaffold layers, fibers 154, and/or of the cell encapsulation membrane 110, themselves. Such material porosity may be formed by way of the room-temperature based extrusion 3D-printing techniques and corresponding materials and processes incorporated herein by reference.

To promote integration and vascularization with surrounding host tissue, the exterior scaffold may comprise biomaterials that promote the healthy tissue integration and vascularization and, particularly, vascularization to the exterior surface of the cell encapsulating member, or cell encapsulation membrane. As noted above, the biomaterials increase efficacy and efficiency of encapsulated cell manufactured factors and promote encapsulated cell health and longevity. The exterior scaffold, or portions thereof, may be pre-embedded with therapeutic molecules, biochemical factors, drugs, etc. to promote such initial vascularization, cell survival, biological targeting, etc. In some examples, the entire device may comprise biomaterials (e.g., the exterior scaffold, one or more fibers, the port, the cell encapsulation membrane, the supports, the bladder walls, the chamber walls, a combination thereof, a portion thereof, or the like). While the interior components, or regions, of the device may or may not comprise biomaterials it is important for the exterior components or regions of the device to comprise biomaterials that readily integrate and vascularize with surrounding tissues of a patient, or host. While the interior components or regions of the device may comprise biomaterials they may not directly interact with the surrounding tissues but, yet, it may still be preferrable in some examples that the interior components or regions still comprise biomaterials with good tissue integration properties, because the exterior of the device may (intentionally or unintentionally) biodegrade or wear down over the course of an implant period into a patient, or host. Thus, the remaining interior components of the device may be directly exposed to the surrounding tissue. Biomaterials are capable of being maintained and survive the extrusion and formation process in view of, for example, the room-temperature based extrusion 3D-printing techniques and corresponding materials and processes described and incorporated by reference herein. It is contemplated herein that any area or regions of the device may comprise biomaterials while other areas or regions of a device may not. Such variations, and the materials relied on therein, are further developed below and may be based on a particular purpose or use or as required for compatibility with the patient, or host, and/or based on interaction with the fluids and/or cells further loaded therein.

Figure 3:
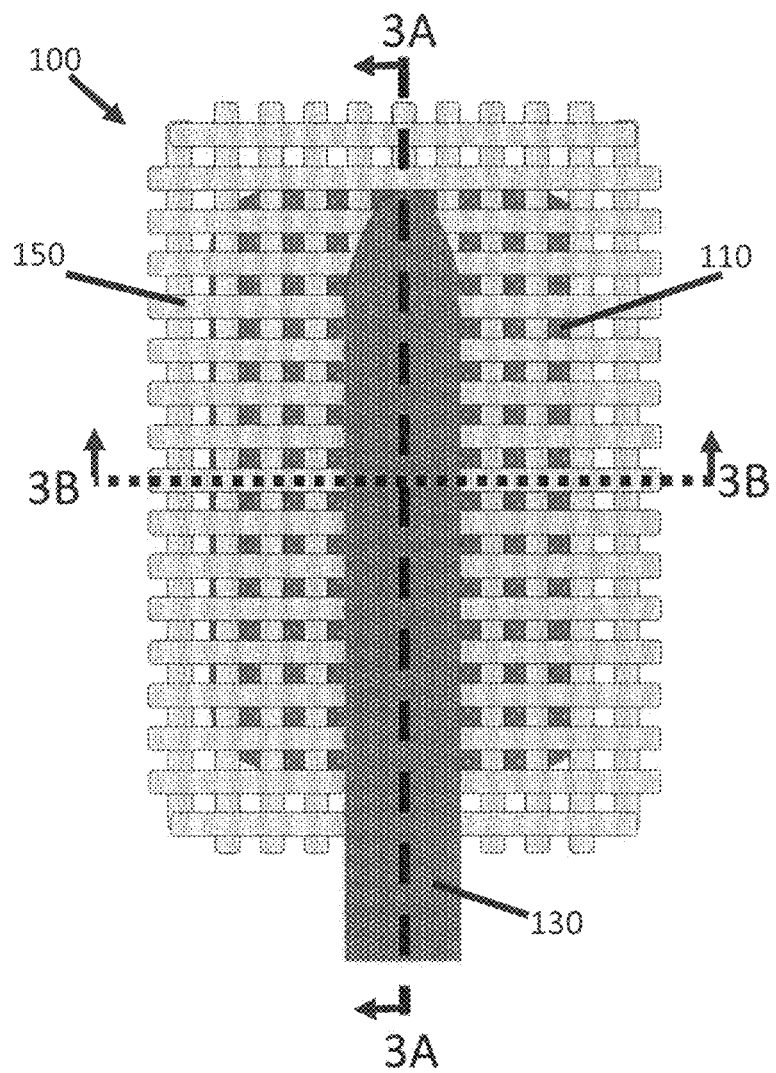
FIG. 3 is a digital representation of a top view of a representative example of a Cell Encapsulation System (CES) device with an injection port extending through the device that additionally protrudes from the top to facilitate easier loading into the device, in accordance with an example of the disclosure.

Turning now to FIG. 3, a digital representation of a top view of a representative example of a CES device is illustrated. An injection port 130 protrudes from a top side of the device 100. Like FIGS. 2 and 2A-2C, the materially porous solid cell encapsulation membrane 110 is provided within an exterior scaffold 150 and forms a bladder and/or one or more chambers therein. The injection port 130 extends through the device 100 and protrudes from the top to facilitate easier loading of fluid and/or cells into the device 100. By example, the thickness of the cell encapsulation membrane 110 and/or the chamber(s) (as illustrated by, at least, FIGS. 4A-4D) may be quite thin (e.g., 20-500 μm). In contrast, the diameter of a needle of a syringe used for injection (including interior open diameter plus the outer material diameter) may be greater than the thickness of the cell encapsulation membrane 110 the bladder, and/or the chamber(s) therein, such as when a 600 μm needle may be used. By pushing a larger diameter needle into a smaller volume chamber(s) and/or a smaller volume bladder the chamber(s) and/or the bladder may be destroyed, thereby exposing the volume of the chambers and/or the bladder and contents therein. Extruding the port 130 from the top surface of the device 100 provides more height, or thickness, to the loading region, allowing a standard needle (which may be thicker than the majority of the volume of the bladder and/or the one or more inner chambers) to be used to load cells. Accordingly, the volume of the bladder and/or the one or more inner chambers, themselves, need not be increased, yet they may be increased based on a particular application if so desired. Comparatively, some examples do not have a port 130 extending, or extruding, from the top surface of the device and the exterior scaffold may fully surround any such features. Hence, numerous variations are contemplated herein. By example, a CES device 100 may comprise multiple ports controlling loading into separated bladders and/or one or more chambers. This allows for distinct loading at physically separated spaces. Distinct loading may be based upon quantity and/or may be based upon loading implemented as different moments in time relative pre-implantation and/or after implantation within a host. Such CES devices may additionally, or alternatively, be symmetrical.

Figure 3A:
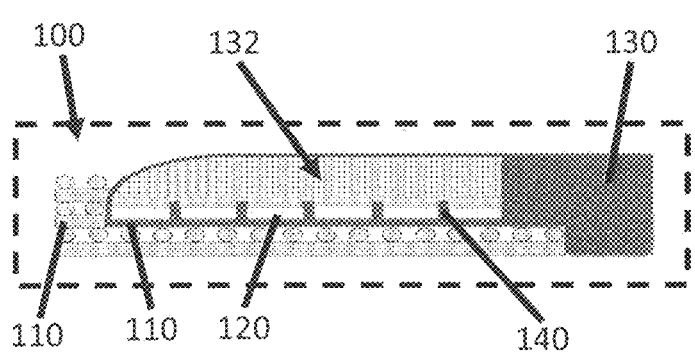
FIG. 3A is a cross-section of the representative example of the device of FIG. 3 taken at line 3A-3A of FIG. 3, in accordance with an example of the disclosure.
Figure 3B:
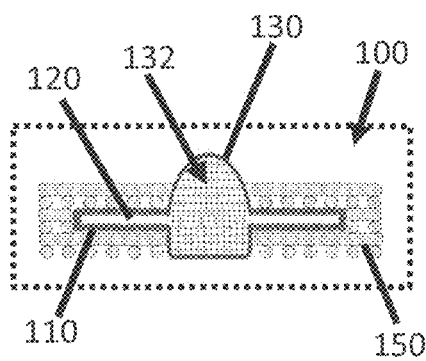
FIG. 3B is a cross-section of the device of FIG. 3 taken at line 3B-3B of FIG. 3, in accordance with an example of the disclosure.

Turning now to FIGS. 3A and 3B which are cross-sections of FIG. 3, the port 130 geometry also guides the needle into the device by keeping it centered within the interior of the port 130. With reference to the cross-sections of FIGS. 3A and 3B, the port 130 geometry keeps the needle aligned in the same plane as the device 100. While the port 130 material itself may be of the same material as other features of the device 100, and may be amenable to puncturing with a needle, the architecture of the port 130 is designed to guide the movement of the needle through the device 100 by providing an interior pathway without requiring puncturing or by providing a lesser degree of resistance when punctured than that encountered when puncturing a needle through a material of a different arrangement. Specifically, the interior of the port 130 is 3D-printed such that it has additional porosity forming an interior pathway 132. The porosity of the interior pathway is independent of and distinct from the porosity of the adjacent material itself. The porosity may be designed such that there are more pore channels that align the length of the port 130. Internal porous supports 140 may additionally be provided along the cell encapsulation membrane 110 at the port 130. In FIG. 3A the internal porous supports 140 are perpendicular to the port length. Such internal porous supports 140 initially separate chamber(s) 120 within the bladder formed by the cell encapsulation membrane 110 from one other (as also further described below). Additionally, the periphery of the port 130, which overlaps the chambers 120 of the bladder formed by the cell encapsulation membrane 110, may be fully open (no boundary between the sides of the port and the surrounding chambers 120 or bladder formed by the cell encapsulation membrane 110). However, below and above the regions where the port 130 overlaps with the chamber(s) or bladder formed by the cell encapsulation membrane 110, the port periphery is printed solid (and may comprise a material that is nano-micron porous, as defined herein).

As noted above, while the material may be same material utilized across each of the features of the device, the architecture of the material, based on the extrusion of the material, may be modified to accommodate a particular function or purpose within the device. There may be multiple variations in the architecture of the material across several parts, regions, and/or features of the device (e.g., bladder, chambers, material porosity, scaffold porosity, port, etc.). In particular, each part, or feature, of the device may be printed in an independent arrangement but simultaneously with each other. This allows for complex designs that are architecturally distinct while still retaining embedded parts. Notably, the cell encapsulation membrane and/or the chamber walls are printed as a materially porous solid. Materially porous solid, as defined herein, means no spacing between adjacent fibers. Yet, the materially porous solid materials may themselves comprise nano-micron porosity therein. Thus, while much of the device may be printed with intentionally designed porosity, by way of the spacing between the extruded fibers (e.g., the exterior scaffold, structural porosity, etc.), the exterior of the cell encapsulation membrane and/or the chamber(s) are intentionally designed to be solid (but with nano-micron material porosity that will allow a degree diffusion into and out of the exterior of the cell encapsulation membrane and/or the chamber(s) while maintaining any cells therein). Additionally, the solid nature of the exterior of the cell encapsulation membrane and/or the chamber(s) prevents vasculature from penetrating into the chamber itself while still allowing vasculature to get very close to cells contained within the chamber(s) and/or cell encapsulation membrane. Finally, the material characteristics are such that the solid top layer of the cell encapsulation membrane can span the large gaps that make up separate chamber volumes, therein, without significant sagging or without collapsing into the chamber(s). In examples, the 3D-printing technique itself may not change regardless of the architecture being printed. Instead, the 3D-printing technique utilized herein provides for the very complex architecture of the systems and device herein. In other examples, not only may the architecture vary across the device, but the material may additionally vary across the device.

Figure 4A:
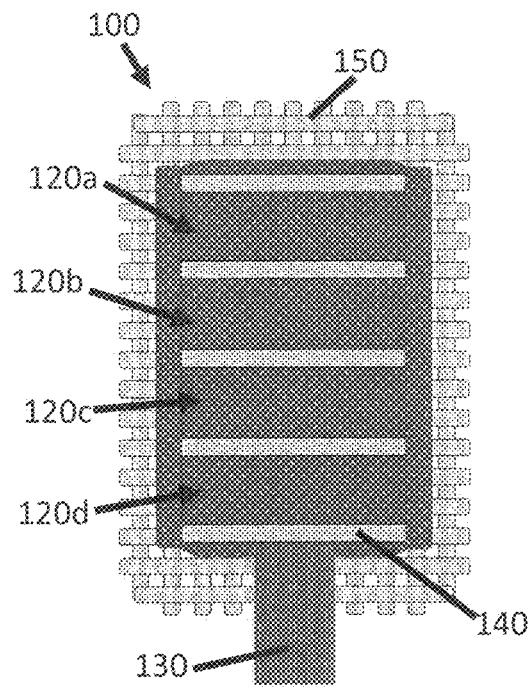
FIGS. 4A-4D are cross-sectional views of the representative example of an injection port and a progression of a process of filling the Cell Encapsulation System (CES) device, where
Figure 4B:
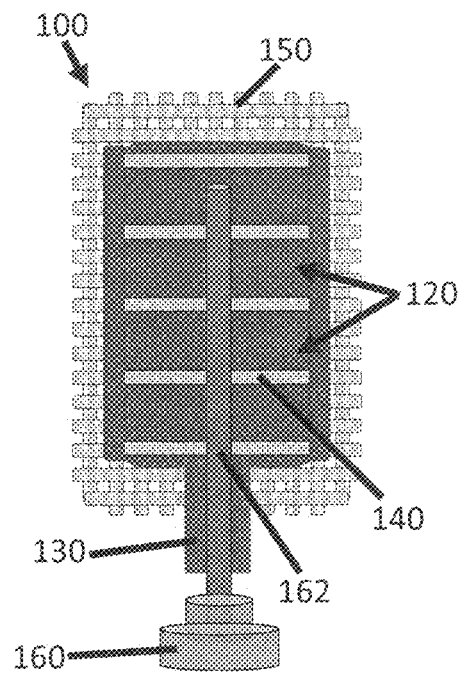
Figure 4C:
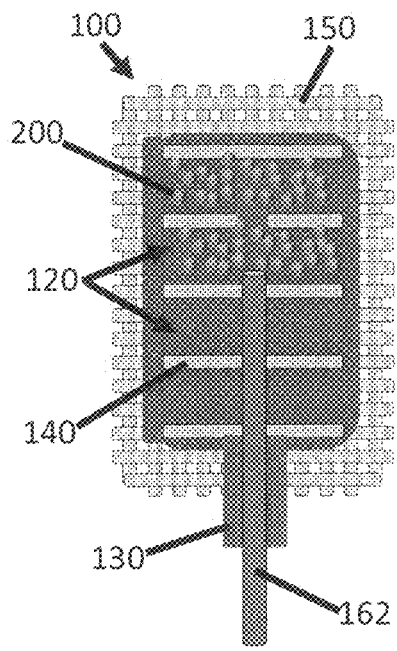
Figure 4D:
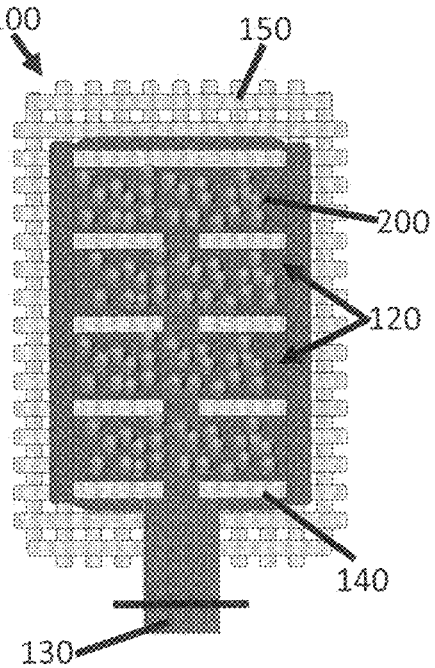

Turning now to FIGS. 4A-4D. FIGS. 4A-4D illustrate cross-sections of a CES device with chamber(s) 120 of the cell encapsulation membrane 110 being filled with cells 200. Such cross-section being perpendicular to the cross-section of FIG. 3A, also extending the length of the CES device. In FIG. 4A a cross-section of the CES device is illustrated with a cell encapsulation membrane 110 positioned within an exterior scaffold 150. A port extends from one end of the cell encapsulation membrane 110 and into the cell encapsulation membrane 110 and, more specifically, into chambers(s) 120a-120d of the cell encapsulation membrane 110. The chambers are separated by internal porous supports 140 that may be punctured by a needle of a syringe. Turning to FIG. 4B, a needle 162 of a syringe 160 is inserted through the port 130 and punctures the internal porous supports 140 between the chambers 120a-120b. In FIG. 4C, fluid and/or cells 200 are loaded into the chamber(s) 120a-120d of the cell encapsulation membrane 110, progressing from the back of the cell encapsulation membrane towards the front of the cell encapsulation membrane as the needle 162 of the syringe 160 is removed. Finally, in FIG. 4D, the chamber(s) 120a-120d are filled with fluid and/or cells and the needle 162 of the syringe 160 has been removed. Upon extraction of the needle 162 of the syringe 160, the end of the port 130 may be mechanically and/or thermally pinched to seal the cells therein. Due to the nano-micron porous (and thus, rough) nature of the material forming the port 130, pinching causes the contacting material of the port 130 to become physically caught on itself (such as, for example, a micro hook-and-loop). Accordingly, pinching results in an opening of the port 130 to become sealed. However, in some applications, such sealing may not be strong enough and heat may be additionally, or alternatively, applied to cause the materials (e.g., thermoplastic materials) to melt and fuse together at that particular location, closing off the opening of the port 130.

Figure 5A:
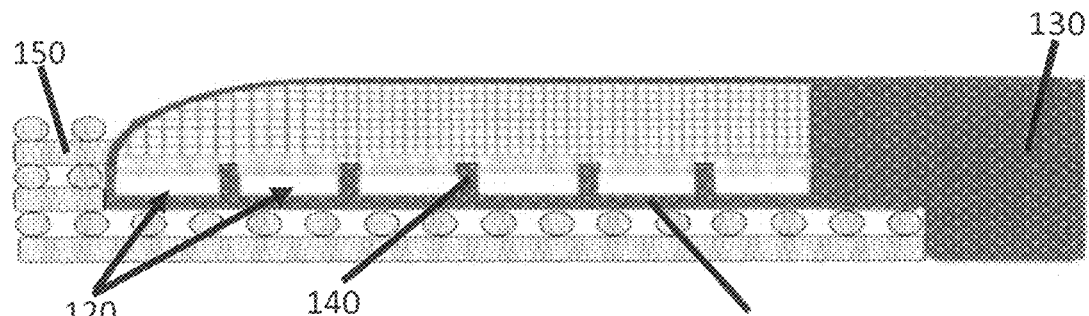
FIGS. 5A-5D are cross-sectional views taken the length of a representative example of a Cell Encapsulation System (CES) device, along the same plane as FIG. 3A, further illustrating the filling process where
Figure 5B:
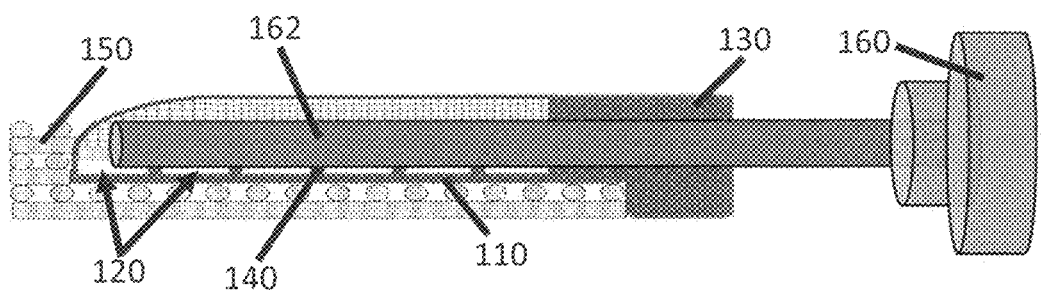
Figure 5C:
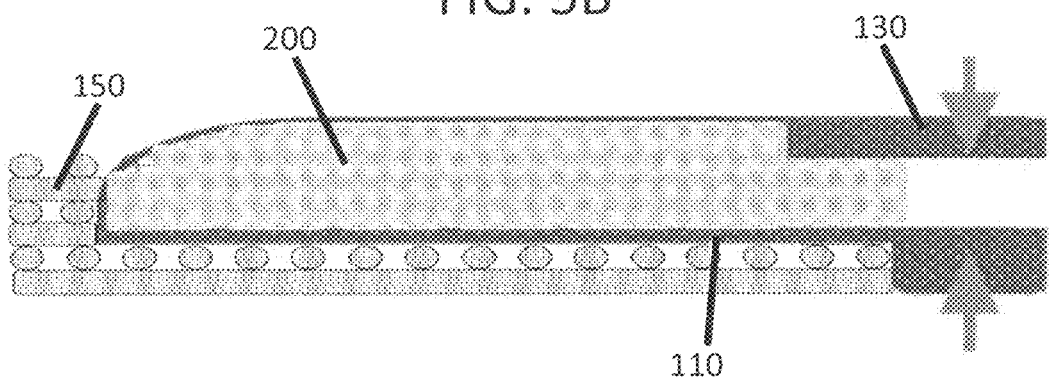
Figure 5D:
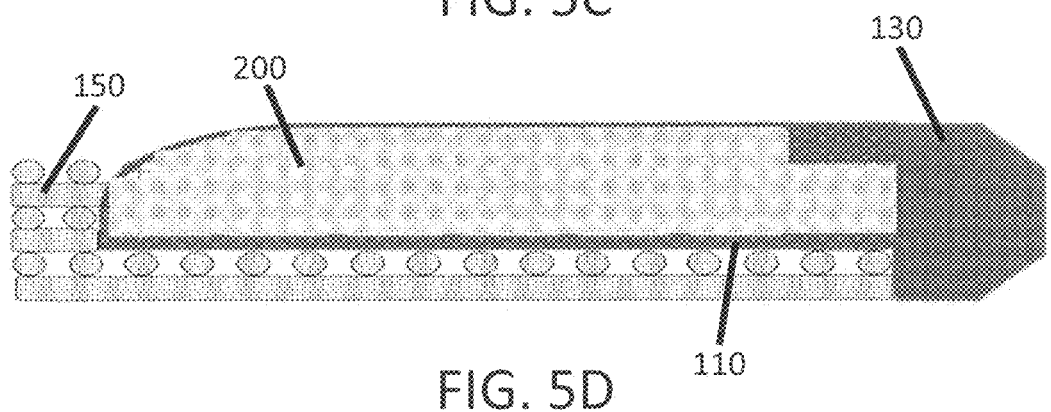

FIGS. 5A-5D illustrate cross-sections, perpendicular to those of FIGS. 4A-4D (similar to the cross-section of FIG. 3A), of the CES device with chamber(s) 120 of a bladder formed by the cell encapsulation membrane 110 prior to filling with cells (FIGS. 5A-5B) and after filling with cells 200 (FIGS. 5C-5D). In FIG. 5A, the CES device is illustrated with a bladder formed by the cell encapsulation membrane 110 positioned within an exterior scaffold 150. A port 130 extends from one end into the bladder formed by the cell encapsulation membrane 110 and, more specifically, into chambers(s) 120 of the bladder formed by the cell encapsulation membrane 110. The chambers are separated by internal porous supports 140 that may be punctured by a needle of a syringe. Turning to FIG. 5B, a needle 162 of a syringe 160 is inserted through the port 130 and punctures the internal porous supports 140 between the chambers 120. In FIG. 5C, fluid and/or cells 200 have been loaded into the chamber(s) 120 of the bladder formed by the cell encapsulation membrane 110. Finally, in FIG. 5D, the chamber(s) 120 are filled with fluid and/or cells and the end of the port 130, extending from the exterior scaffold 150, has been mechanically and/or thermally pinched to seal the cells therein and is ready for use.

The bladder formed by the cell encapsulation membrane and/or the chamber(s) therein exist to contain loaded cells. The CES device may comprise a single chamber, several chambers, or multiple chambers. The CES devices of the present disclosure may comprise a single chamber. The CES devices of the present disclosure may comprise multiple distinct chambers. The CES devices of the present disclosure may comprise multiple connected chambers. The CES devices of the present disclosure may comprise multiple non-connected chambers. The CES devices of the present disclosure may comprise multiple non-connected and/or connected chambers. The CES devices of the present disclosure may comprise multiple, discrete, orthogonal chambers. The CES devices of the present disclosure may comprise concentric chambers.

Multiple chambers may be provided within the bladder formed by the cell encapsulation membrane in lieu of a single chamber to provide a supporting structure within the cell encapsulation membrane based on size, application, and particular use. By example, a single chamber (i.e., a bladder) may swell unevenly during loading and/or after implantation. This may result in the chamber "bowing" and resulting in longer diffusion distances to the exterior of the device for cells located in the center of the single chamber (i.e., bladder) (such as, for example, at regions within the bladder formed by the cell encapsulation membrane having the largest "bow"). Smaller, more numerous chambers may be provided within the bladder to combat this. By example, the smaller chambers may be bound by separating side walls or internal porous supports. Accordingly, the smaller chambers would not be as susceptible to "bowing" or swelling during filling and/or implantation. Such chamber arrangements, or variations, ensure more homogeneity with respect to cell distance from the exterior of the device and provide for consistent factor diffusion into and out of the chambers of the bladder.

The CES device of the present disclosure may be produced in a wide range of sizes. A device may be as small as 600 μm in any direction (i.e., lateral dimensions). Such a device may be printed using a limited number of fibers. By example, three (3) 200 μm fibers may be placed in a side-by-side arrangement, with no spacing therebetween, and, additionally, stacked three (3) 200 μm fibers high with a void for a bladder formed therein to a length additionally limited to 600 μm. In contrast, the device may be printed as laterally large as desired for a particular application. By example, the only limitation to increasing the lateral size is the size of the manufacturing platform used. Such flexibility provides the CES device of the present disclosure the availability for use across numerous applications with very little limitations in size.

Internal porous support(s) may span the entire thickness of a bladder and/or one or more chambers. Internal porous support(s) may span the entire length of a bladder and/or one or more chambers. Internal porous support(s) may be of the same material or of a different material than the encapsulating bladder and/or one or more chambers. Internal porous support(s) may swell to increase the chamber volume. Alternatively, internal porous support(s) may restrict a bladder and/or chamber from swelling. Internal porous support (s) may prevent a bladder and/or chamber from being compressed and/or from being crushed by external forces or limit/restrict compression of the bladder and/or chamber. While the internal porous support(s) may operate as separating sidewall(s) that divide a bladder and/or chamber into multiple chambers, in some examples, the internal porous support(s) may extend only a partial length and/or partial thickness of a bladder and/or chamber, thereby, not fully dividing a bladder and/or chamber into separate chambers. As noted above, the bladder and/or one or more chambers of the CES devices of the present disclosure may be expandable upon loading and/or after loading. As also noted above, the bladder and/or one or more chambers of the CES devices of the present disclosure may resist expansion at loading and/or upon loading.

Figure 6A:
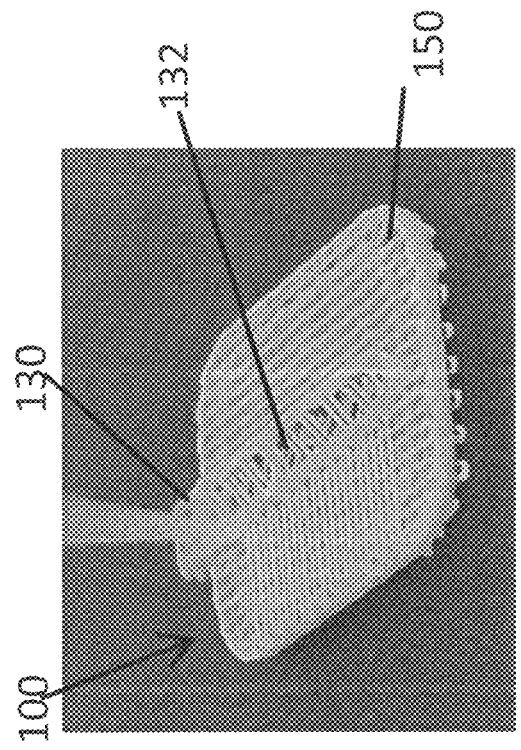
FIGS. 6A-6D are progressive images of a representative example of a Cell Encapsulation System (CES) device being 3D printed with an exterior scaffold layer with an injection port extending into a materially porous solid cell encapsulation membrane printed therein, where
Figure 6B:
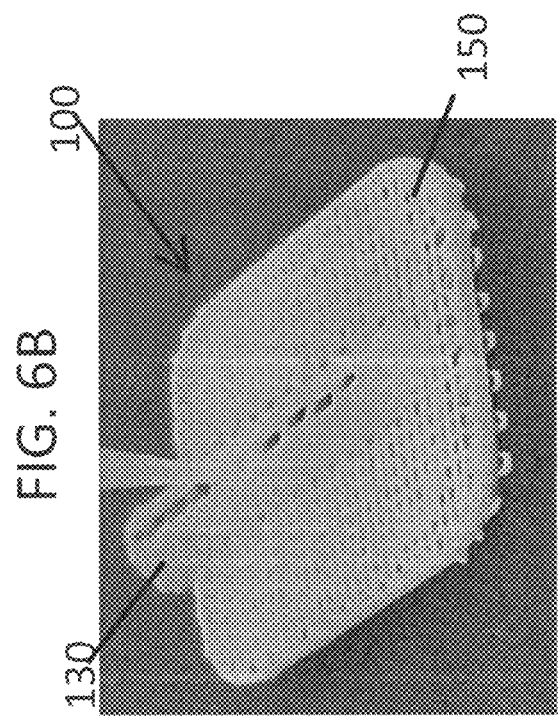
Figure 6C:
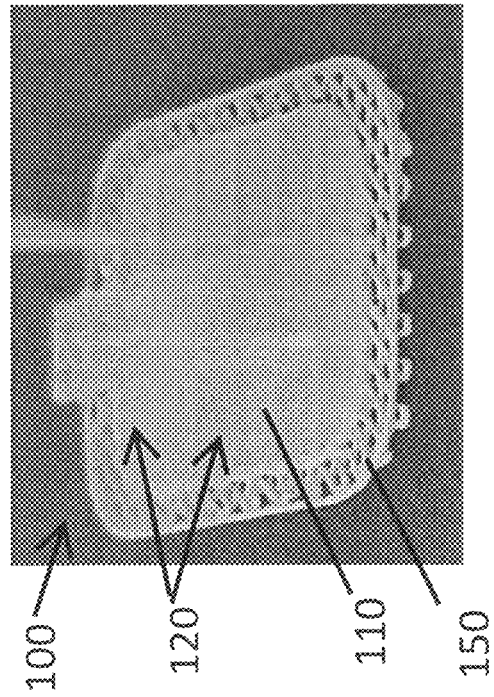
Figure 6D:
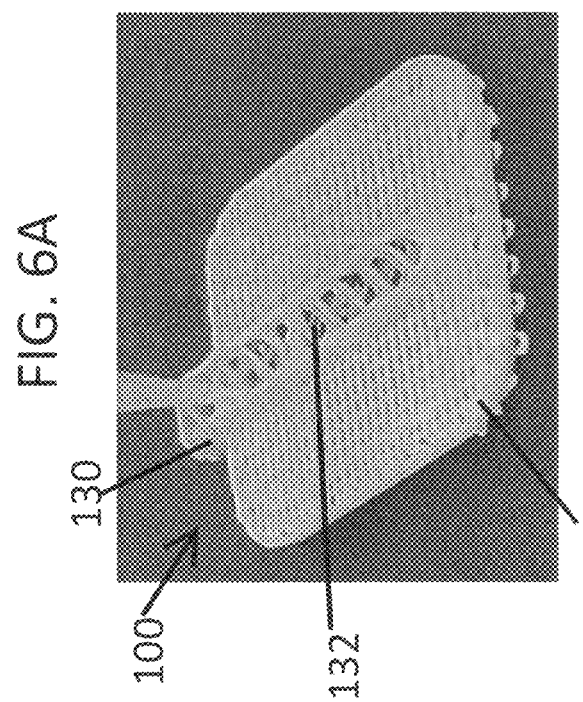

Turning now to FIGS. 6A-6D, the formation of or the 3D-printing extrusion of a CES device 100 is illustrated. In FIG. 6A, the base of a bladder formed by a cell encapsulation membrane 110 and chambers 120 therein are constructed within the exterior scaffold 150. FIG. 6B illustrates a completed cell encapsulation membrane being fully enclosed within the exterior scaffold 150 with a port 130 extending from the center of the bladder, the chambers 120 therein, and the exterior scaffold 150. FIGS. 6B and 6C further illustrate the internal porosity of the port 130 being 3D-printed such that a pathway 132 is formed through the port 130. Finally, FIG. 6D illustrate the pathway 132 being enclosed by completing the 3D-printing of the remainder of the port 130.

Figure 6E:
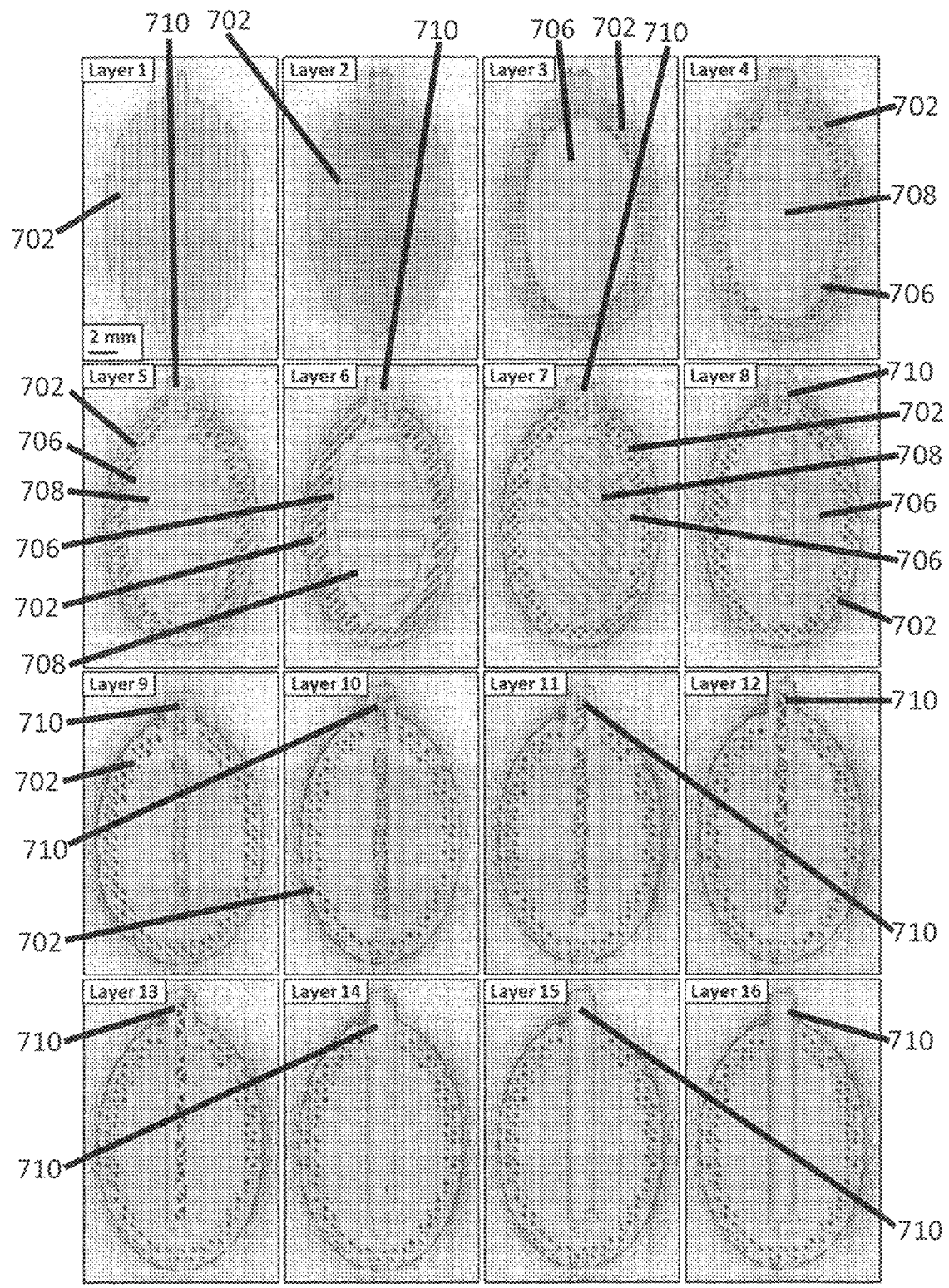
FIG. 6E also shows progressive images of layering a representative example of a Cell Encapsulation System (CES) device in Layers 1-16 and corresponding to Table 1, in accordance with an example of the disclosure.

FIG. 6E further illustrates progressive layering undertaken to form a CES device 100 in greater detail by Layers 1-16. Layers 1-16 further correspond to formation of features as identified in Table I below:

TABLE 1

| Layer # | Component Description |
|---|---|
| Layer 1 | Pro-integrative scaffold (702) |
| Layer 2 | Pro-integrative scaffold (702) |
| Layer 3 | Pro-integrative scaffold (702); Encapsulating membrane (704) |
| Layer 4 | Pro-integrative scaffold (702); Encapsulation chambers (706) + supports (708); Injection Port (710) |
| Layer 5 | Pro-integrative scaffold (702); Encapsulation chambers (706) + supports (708); Injection Port (710) |
| Layer 6 | Pro-integrative scaffold (702); Encapsulation chambers (706) + supports (708); Injection Port (710) |
| Layer 7 | Pro-integrative scaffold (702); Encapsulation chambers (706) + supports (708); Injection Port (710) |
| Layer 8 | Pro-integrative scaffold (702); Encapsulation membrane (704); Injection Port (710) |
| Layer 9 | Pro-integrative scaffold (702); Injection Port (710) |
| Layer 10 | Pro-integrative scaffold (702); Injection Port (710) |
| Layer 11 | Injection Port (710) |
| Layer 12 | Injection Port (710) |
| Layer 13 | Injection Port (710) |
| Layer 14 | Injection Port (710) |
| Layer 15 | Injection Port (710) |
| Layer 16 | Injection Port (710) |

In examples, the material the CES device is formed from is fully or in part of Fluffy-X™ materials (nano-micron porous polymers) as described in U.S. Patent Publication No. 2020/0353129 A1 entitled WATER-SOLUBLE SALT PARTICLE CONTAINING COMPOSITIONS AND POROUS MATERIALS MADE THEREFROM, filed 29 Apr. 2020, which is herein incorporated by reference in its entirety. Additionally, or alternatively, the material the CES device is formed from is fully or in part of Hyperelastic Bone® materials as described in U.S. Pat. No. 11,654,214 entitled CERAMIC-CONTAINING BIOACTIVE INKS AND PRINTING METHODS FOR TISSUE ENGINEERING APPLICATIONS, filed 26 Apr. 2018, which is herein incorporated by reference in its entirety. By example, a device intended for implantation into or onto the surface of boney tissue may have an exterior comprising Hyperelastic Bone® to promote integration with boney tissue, while the interior comprises Fluffy-X™, inhibiting bone formation on the inside of the device.

Additionally, or alternatively, the material the CES device is formed from is fully or in part of self-gelling materials as described in U.S. Patent Publication No. 2022/0401630 A1 entitled METHOD FOR FABRICATION OF ADDITIVELY MANUFACTURED, SELF-GELLING STRUCTURES AND THEIR USE, filed 18 Mar. 2022, which is herein incorporated by reference in its entirety. Additionally, or alternatively, the material the CES device is formed from is fully or in part of electrically conductive biomaterials as described in U.S. Pat. No. 10,350,329 entitled GRAPHENE-BASED INK COMPOSITIONS FOR THREE-DIMENSIONAL PRINTING APPLICATIONS, filed 15 Oct. 2015, which is herein incorporated by reference in its entirety. The material the CES device is formed from may be fully or partially of magnetic field response materials. An example may include ferromagnetic metals, or the like. Additionally, or alternatively, the material the CES device is formed from may be fully or partially of piezo-responsive materials. An example may include piezoelectric, piezomagnetic, piezo-thermal materials, a combination thereof, or the like. In examples, the CES device, and the encapsulated cells therein, may be mechanically, electrically, magnetically, thermally, etc. stimulated (and, thus, the cells therein may be mechanically, electrically, magnetically, thermally, etc. stimulated) to induce a particular encapsulated cell response. Examples of such responses may be an increase in production of target factors, a decrease in production of target factors, etc. By example, an external magnet may be externally applied periodically and mechanically "pulse," squeeze, or manipulate the device and/or the encapsulated cells. The material the CES device is formed from may comprise genetic material (plasmids, single stranded DNA, double stranded DNA, mRNA, tRNA, rRNA, or the like). The material the CES device is formed from may comprise functionalized nano- and microparticles capable of responding to local environmental stimuli. The material the CES device is formed from may comprise nano- or micro-machined mechanical, electronic, photonic, or a combination thereof. The CES device's surface may also be chemically modified. By example, the chemically modified CES device surface comprises surface functionalization with click chemistries, proteins, genetic materials, nanoparticles, microparticles, adhesion, a combination thereof, etc. In examples, the material the CES device is formed from may be any combination of the material noted herein. The CES device is not a hydrogel but may contain hydrogel components. See, for example, U.S. Patent Publication No. 2022/0401630 A1, as incorporated by reference above.

In versions of the above examples, the material microstructure of a CES device may vary between device components, may vary within a single device component, or a combination thereof. The CES device may comprise a single material chemistry (i.e., a singular type of polymer or composite). The CES device may comprise multiple material chemistries (i.e., different compositions along multiple components and/or different compositions within the same component). The CES device may be made of highly distinct materials (e.g., exterior integrating scaffold material may comprise components intended to target surrounding tissue, while the interior material components are not tissue specific). In an example, the CES device may comprise a material composition that remains constant while the material microstructure changes. The CES device may comprise added therapeutic molecules, factors, drugs, biochemistries (distinct from the contained cells). The CES device may be designed to promote beneficial, tissue-specific interactions (i.e., designed for subdermal use, designed for implantation on surface of an organ, etc.). The CES device may be designed to promote local or system delivery of the target factor. The CES device may be designed to work in tandem with separately manufactured CES devices containing the same or different encapsulated cells. It is contemplated herein, that while the material or material microstructure of a CES device may vary across components, the CES device is continuously printed and/or printed in a single step. For example, each of the components of a CES device may be continuously printed together on a 3D-printer that has the capability to select different materials for different components and printing the components continuously and all together in parallel to yield a single continuous device printed in a single step. Accordingly, the CES device may be a multi-component device with varied material compositions across components or even within a single component.

FIGS. 7A-7F and 7H-7K illustrate a CES device 100 with fluid and/or cells 200 being injected, or loaded, therein by a loading device. The loading device of FIGS. 7A-7F and 7H-7K is a needle 162 of a syringe 160. In FIG. 7A, the needle 162 of the syringe 160 is inserted into a port 130 within a CES device 100 to access a bladder and/or one or more chambers formed by the cell encapsulation membrane 110 that is within an exterior scaffold 150 of the CES device. In the progression of FIGS. 7B-7F and 7H-7I, the fluid and/or cells 200 are loaded therein and progressively fill the bladder and/or the one or more chambers formed by the cell encapsulation membrane 110 wherein the cells 200 are distributed therein. FIG. 7J illustrates the removal of the needle 162 of the syringe 160 from the CES device. Finally, FIG. 7K illustrates the port 130 being pinched to seal the cells 200 within the bladder and/or the one or more chambers formed by the cell encapsulation membrane 110 after removal of the needle 162 of the syringe 160 from the CES device. Additionally, or alternatively, the injection port may be cut and sealed using a scalpel, razor blade, scissors, shears, or similar instrument with or without the aid of heat (cauterizing). Additionally, or alternatively, the injection port may be sealed using ultrasonic welding. Additionally, or alternatively, the injection port may be sealed by cutting and cauterization using a laser or similar optical method.

A loading device may be a syringe, syringe needle, flexible tubing, pump, automated system, a combination thereof, or the like. By example, the CES device may comprise an injection port-to-tubing connector that a loading device may fluidly connect to. The connector may be separately made and connected to the injection port (i.e., made as a separate part and added separately to the CES device injection port). The connector may be fabricated using the same manufacturing steps and materials as the CES device. The connector may be created with, and as a part of, the construction of the CES device. In the example of loading using a needle, the CES device may be loaded with a needle that is beveled, non-beveled, tapered, or chamfered. The CES device may be loaded with a needle that is 30 Ga or larger. Alternatively, the CES device may be loaded by flexible tubing, manually by a syringe, semi-manually by a user-controlled pump, or a pre-programed automated system. By example, a pre-programmed automated system for loading may measure one or more of load density, cell viability, and cell functionality in real time to control loading.

Figure 12A:
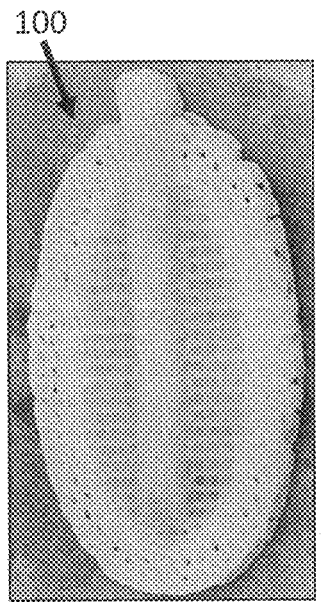
FIGS. 12A-12D are top views of representative photographic images of Cell Encapsulation System (CES) devices with colored dye and particles loaded into the devices, where
Figure 12B:
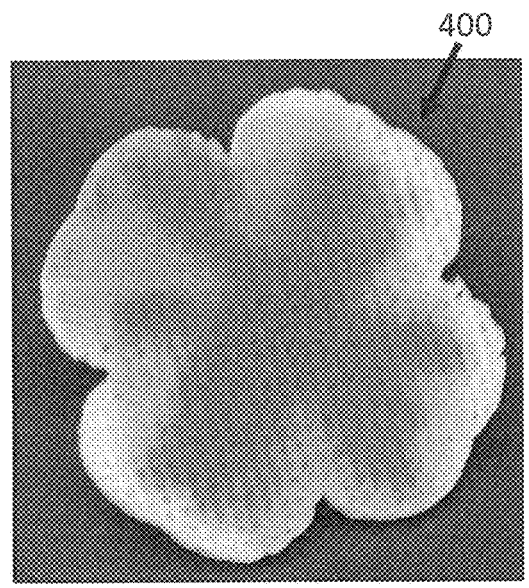
Figure 12C:
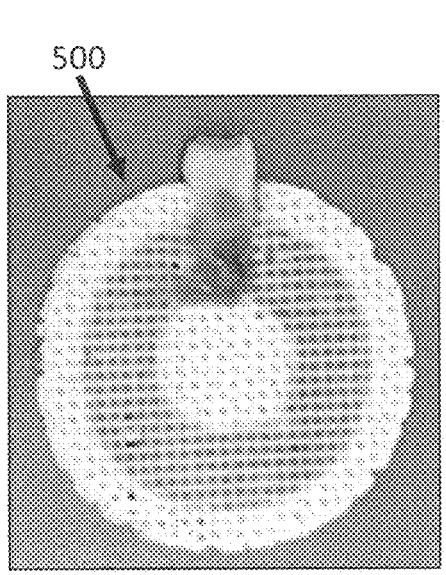
Figure 12D:
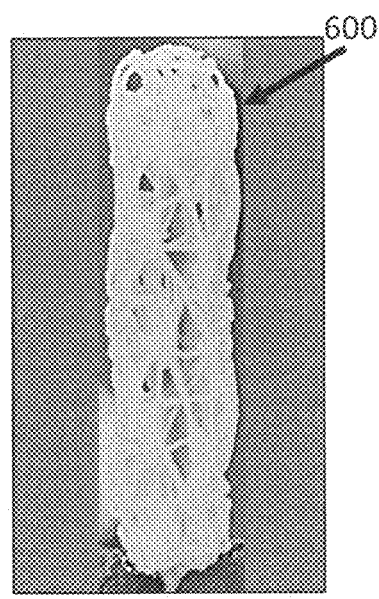

The examples of FIGS. 7A-7K illustrate that the loading of the cells into the bladder and/or the one or more chambers formed by the cell encapsulation membrane may be visually observable. Because the entire composition (material) of the device may comprise nano-to-micron-scale interconnected porosity the entire device will absorb and distribute moisture throughout the entirety of the device. Thus, when the fluid and/or cells are loaded into the bladder and/or the one or more chambers formed by the cell encapsulation membrane the fluid and/or cells will serve as a visual identifier of the progression of loading of the cells into the bladder and/or chamber(s). Because the inner bladder and/or chamber(s) are enclosed by material with porosity that is too small for cells to pass through, the inner bladder and/or chambers will fill with both the fluid (media, blood, etc.—whatever the medium is used to load the cells) and the cells. Further, if the cells have a color/visual difference distinct from the fluid medium used to load them, it is possible to also visually observed when individual bladder and/or chambers are filled with cells. This can be assisted by shining a light through the device as it is being filled, as the material(s) comprising the device are somewhat translucent (i.e., backlighting the device during filling can assist with filling). Examples of this are provided in the photographic images of FIGS. 12A-12D, wherein colored dye and particles have been injected within a single-lobe CES device 100 configuration of FIG. 12A, a four-lobe CES device 400 configuration of FIG. 12B, a donut CES device 500 configuration of FIG. 12C, and a tube template CES device 600 configuration of FIG. 12D. Each configuration described in greater detail below. Body fluids from a host (e.g., media, blood, etc.) may additionally absorb into the device upon implantation from a host. This may further promote healthy integration of native host tissue and vasculature with the device exterior and mitigating acute and chronic encapsulation/fibrosis and other non-specific immunological response to the implanted device, while further promoting biochemical exchange/transport between the immunologically isolated, encapsulated cells and the host tissue.

The cell encapsulation membrane and/or the scaffold material may consist of a fully biodegradable material or may comprise of a fully biodegradable material. The cell encapsulation membrane and/or the scaffold material may consist of a partially biodegradable material or may comprise of a partially biodegradable material. The cell encapsulation membrane and/or the scaffold material may consist of a non-biodegradable material or may comprise of a non-biodegradable material. The cell encapsulation membrane and/or the scaffold material may consist of a conditionally biodegradable material or may comprise of a conditionally biodegradable material. A conditionally biodegradable material is a material that may be programmed to degrade based on certain conditions or upon a defined exposure. By example, a conditionally biodegradable material may be programmed to degrade based on local pH, temperature, exposure to specific enzymes, a combination thereof, or the like. A cell encapsulation membrane and/or a scaffold material may comprise of one or more of a fully biodegradable material, a partially biodegradable material, a non-biodegradable material, and a conditionally biodegradable material.

As generally described above, it is contemplated the CES device may comprise different geometrically distinct configurations, arrangements, material properties, biomaterials, varying biodegradability, or the like. In other words, the CES device provides architectural complexities. Accordingly, it is contemplated herein the CES device may comprise varying arrangements of the features described above, wherein some features may be absent from arrangement(s), some features may be duplicated in arrangement(s), or a combination thereof. By example, physical placement of separately produced membrane layer(s) may be made within the CES device as the CES device is formed (e.g., 3D-printed). In examples, formation of the CES device (e.g., 3D-printing) may be halted after completion of a particular layer. By example, formation of the CES device may be halted after completion of layer 2 of Table 1, above, and as illustrated by FIG. 6E. Accordingly, a thin membrane or component may be physically positioned or placed on top of layer 2 (essentially creating an independent layer 3). Thereafter, the formation process (e.g., 3D-printing process) may resume. Additional stoppages of the formation of the CES device may occur. By example, the formation process may additionally, or alternatively, stop upon completion of layer 7 of Table 1, above, and as illustrated by FIG. 6E. Additionally, or alternatively, another membrane or component may be physically positioned or placed. Formation (e.g., 3D-printing) may then re-commence thereafter. Due to the nature of the materials described herein the formed material may additionally bond with the separately produced and placed membranes or components. Other layers or films of polymers may be applied to any layer of formation by stopping the formation process (e.g., 3D-printing) at any point by virtue of coating or spraying. By example, the in-process CES device, or component thereof, may be sprayed or coated with a solubilized polymer. The sprayed polymer may be biodegradable or non-biodegradable. In an example, after completion of the formation of layer 3 of Table 1, above, and as illustrated by FIG. 6E, the formation process (e.g., 3D-printing) of the CES device may be paused and the device may be sprayed or coated with a thin coat of a non-biodegradable polymer such as polyethylene, PTFE, polyurethane, polycarbonate, etc. This yields thin coatings of materials on defined layers of the device. Examples may include spraying or coating the solid membrane layers that are formed from biodegradable material with a non-biodegradable polymer. This would create a very thin, additional, non-biodegradable membrane/coating around the primary solid membrane layers of the CES device. Further described below are examples that illustrate additional variations of said architectural complexities. These examples are not intended to limit the overall disclosure but are illustrative of only a small sample of the many possible configurations, arrangements, properties, etc. contemplated herein. Examples are also provided herein to illustrate features related to a particular purpose for a particular medical condition, and reasons therefor.

Figure 1A:
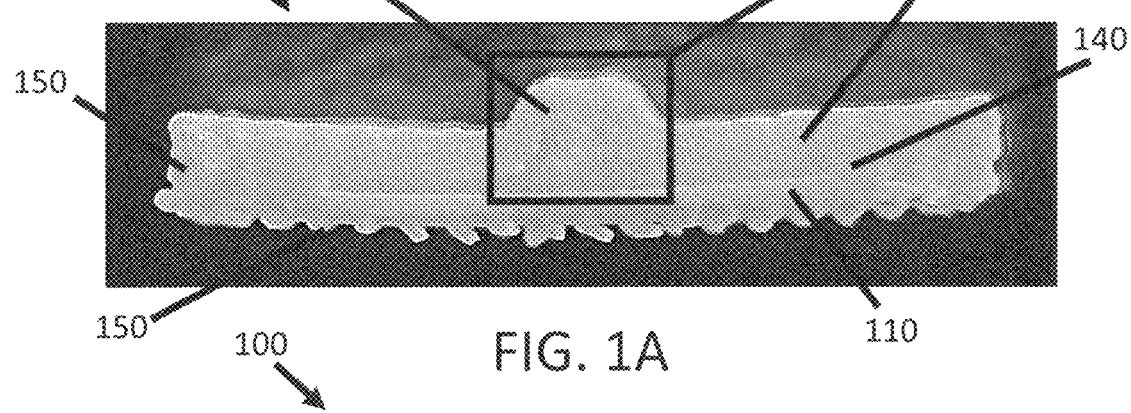
FIG. 1A is photographic image of a cross-section of a Cell Encapsulation System (CES) device taken at line 1A-1A of FIG. 1, in accordance with an example of the disclosure.
Figure 1B:
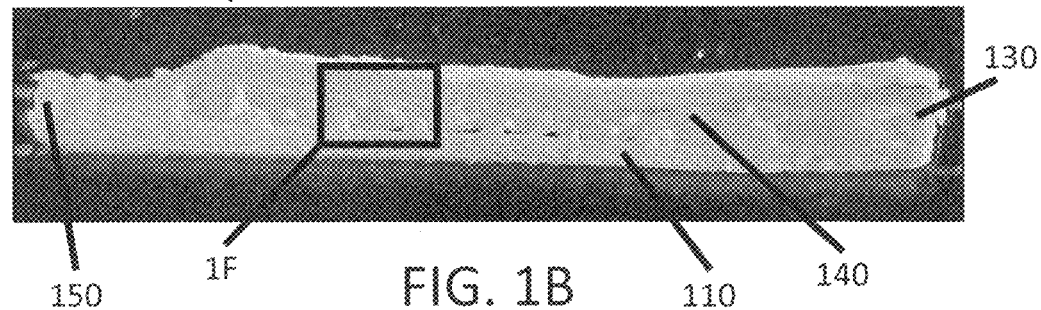
FIG. 1B is a photographic image of a cross-section of a Cell Encapsulation System (CES) device taken at line 1B-1B of FIG. 1, in accordance with an example of the disclosure.
Figure 8A:
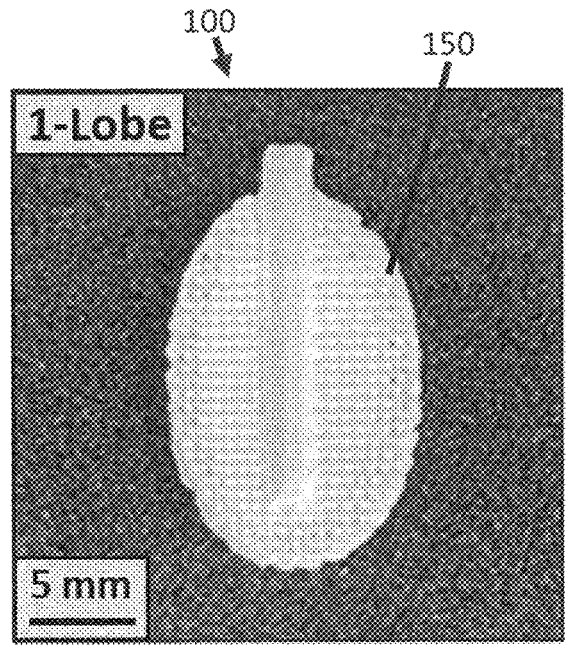
FIG. 8A is a top view of a representative photographic image of a Cell Encapsulation System (CES) in a single-lobe configuration, in accordance with an example of the disclosure.

The examples of a CES device illustrated by the FIGS. 1A-1B, above, may be generally referred to herein as a single lobe configuration. As used herein, a lobe may comprise a bladder and/or one or more chambers formed by the materially porous solid cell encapsulation membrane. A single lobe configuration is, again, illustrated, to scale, in the photo image of a CES device of FIG. 8A for comparative illustration in view of a four-lobe configuration of FIG. 8B, a donut configuration of FIG. 8C, and a tube template configuration of FIG. 8D. As illustrated by FIG. 8A, the CES device 100 may comprise a sub-cell-scale materially porous solid cell encapsulation membrane 110 (as illustrated by FIG. 1B), internal porous supports 140 (as illustrated by FIG. 1B), an injection port 130 (as illustrated by FIG. 1B), and an exterior scaffold 150. While the CES device of FIG. 8A comprises dimensional symmetry, along a longitudinal axis extending its length, it is contemplated herein a single lobe configuration may or may not have dimensional symmetry or may have dimensional symmetry in additional directions.

Figure 8B:
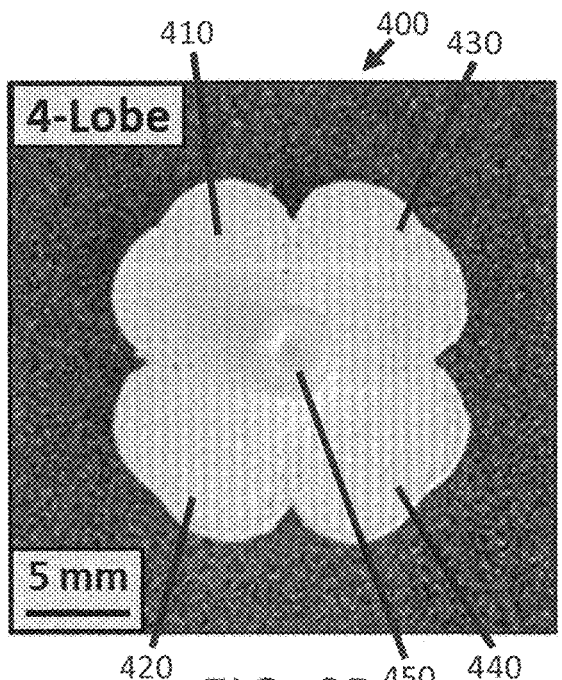
FIG. 8B is a top view of a representative photographic image of a Cell Encapsulation System (CES) in a four-lobe configuration, in accordance with an example of the disclosure.
Figure 9A:
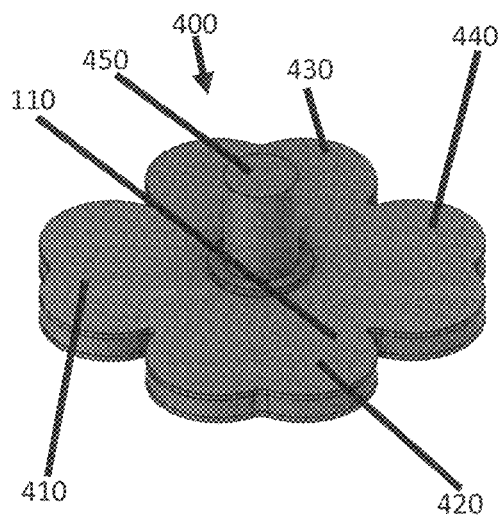
FIG. 9A is a digital representation of a top view of a representative example of a Cell Encapsulation System (CES) device in a four-lobe configuration, in accordance with an example of the disclosure.
Figure 9B:
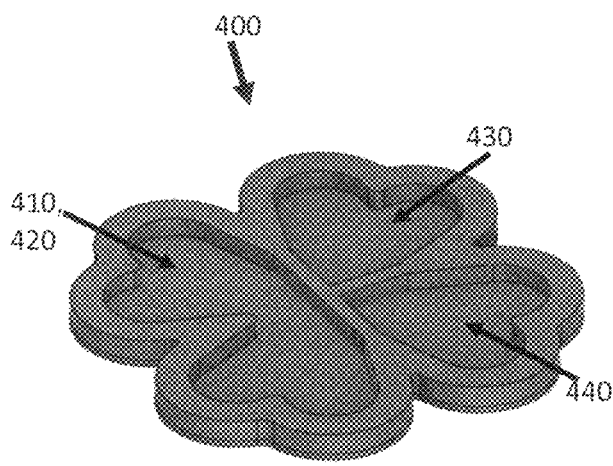
FIG. 9B is a cross-sectional view of a digital representation of a representative example of a Cell Encapsulation System (CES) device in a four-lobe configuration, in accordance with an example of the disclosure.

FIG. 8B illustrates another configuration of a CES device that is generally referred to herein as a four-lobe configuration. The four-lobe configuration of FIG. 8B is a CES device 400 comprising extensions (or lobes) 410, 420, 430, 440 extending from a central core that is, in this instance, the injection port 450. The four-lobe configuration may also support any form of extension from any of the arrangements herein, as contemplated and supported by the present disclosure, regardless of whether it is an extension from a central core, stacked extensions, an extension of another shape, extensions of varying shapes, extensions of the same orientation, extensions of varying orientations, or the like. The CES device 400 of the four-lobe configuration may comprise a sub-cell-scale materially porous solid cell encapsulation membrane 110 (as illustrated by FIG. 1B) in each of a first lobe 410, a second lobe 420, a third lobe 430, and a fourth lobe 440. The CES device 400 of the four-lobe configuration may additionally comprise internal porous supports 140 (as illustrated by FIG. 1B) in each of a first lobe 410, a second lobe 420, a third lobe 430, and a fourth lobe 440. The CES device 400 of the four-lobe configuration illustrates a single injection port 450 that is shared across each lobe of the four-lobe configuration. Specifically, the injection port 450 of the CES device 400 is a single port that accesses all lobes 410, 420, 430, 440 via a central point. In the example of FIG. 8B, the injection port 450 is arranged such that it is a central core of the four-lobe configuration. Additionally, or alternatively, the four-lobe configuration (or multiple lobe configuration) may comprise an injection port (as illustrated by FIG. 1B) in one or more of a first lobe 410, a second lobe 420, a third lobe 430, and a fourth lobe 440 (e.g., some or all lobes of a multiple lobe configuration). In examples, the lobes may be internally connected across the entire device. In other examples, lobes may be selectively internally connected (e.g., only two of four lobes in a CES device may be internally connected in a four-lobe device). In examples, the lobes may be fully internally isolated from each other. In other examples, lobes may be selectively internally isolated from each other (e.g., only two of four lobes in a CES device may be internally isolated in a four-lobe configuration) such as, for example, as illustrated by FIGS. 9A-9B. Internally connected is defined as having encapsulating chambers of respective lobes that are capable of sharing fluid (i.e., openings and/or passages are provided that connect encapsulating chambers across different lobes). Internally isolated is defined as having encapsulating chambers of respective lobes that are not capable of sharing fluid (i.e., there are no openings or passages that connect encapsulating chambers across different lobes). The CES device 400 of the four-lobe configuration may additionally comprise any additional features introduced, generally, herein for a single lobe in one or more of the first lobe 410, a second lobe 420, a third lobe 430, and a fourth lobe 440.

While the CES device 400 of FIG. 8B comprises dimensional symmetry about itself, in addition to dimensional symmetry at each respective lobe, it is contemplated herein the CES device and/or some or all the lobe configurations may or may not have dimensional symmetry or may have dimensional symmetry in multiple directions. In other words, respective lobes of a multiple lobe configuration may or may not have individual-self dimensional symmetry. Multiple lobes may or may not have dimensional symmetry across the device geometry. The four-lobe configuration of FIG. 8B is not intended to limit a multiple lobe CES device to only four lobes. Instead, it is contemplated herein a multiple lobe CES device may comprise any number lobes, of which the four-lobe configuration of 8B is intended to be illustrative.

Still referring to FIG. 8B, the CES device 400 comprises lobes all within the same dimensional plane (e.g., a flat lobed device). It is also contemplated herein a CES device may comprise one or more lobes of a multiple lobe CES device that occupy more than one plane. It is also contemplated herein entire lobes of a multiple lobe CES device may occupy different planes relative other lobes of the multiple lobe CES device. In FIG. 8B, the injection port 450 does not occupy the same plane as the lobe(s) and is said to be out-of-plane. In examples, the injection port may or may not occupy the same plane as the lobe(s) or one or more lobe(s).

Figure 8C:
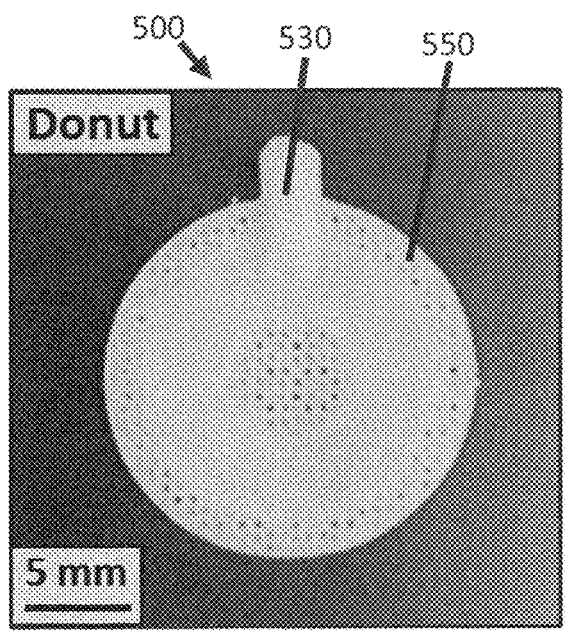
FIG. 8C is a top view of a representative photographic image of a Cell Encapsulation System (CES) in a donut configuration, in accordance with an example of the disclosure.

FIG. 8C illustrates a donut configuration of a CES device 500. The donut configuration illustrates that, while a lobe is relied on above, the CES device 500 may be made of any geometric shape or configuration. Like the lobe configurations, the CES device 500 of a donut configuration may comprise a sub-cell-scale materially porous solid cell encapsulation membrane 110 (as understood by the illustration of FIG. 1B), internal porous supports 140 (as understood by the illustration of FIG. 1B), an injection port 530, and an exterior scaffold 550. The difference between the donut configuration of CES device 500 of FIG. 8C and the lobe configuration of the CES device 100 of FIG. 8A is that the CES device 500 of FIG. 8C comprises a single chamber with a single access through an injection port 530 provided at its perimeter, and not dividing or separating the device into multiple chambers. In contrast, the CES device 100 of FIG. 8A comprises multiple chambers with a single injection port 130 that access all chambers that are otherwise divided by internal porous supports (i.e., internal porous supports as illustrated by FIG. 1B). In the CES device 100 of FIG. 8A the chambers are only connected through the single injection port 130 that is in-plane with the chambers and extends a fully length thereby bisecting the CES device 100 into separate chambers. In contrast, in the CES device 500 of FIG. 8C the chamber is continuous, wherein the injection port 530 is in-plane with the chamber and is positioned at the perimeter of the CES device 500, only partially penetrating the cavity of the chamber.

Figure 8D:
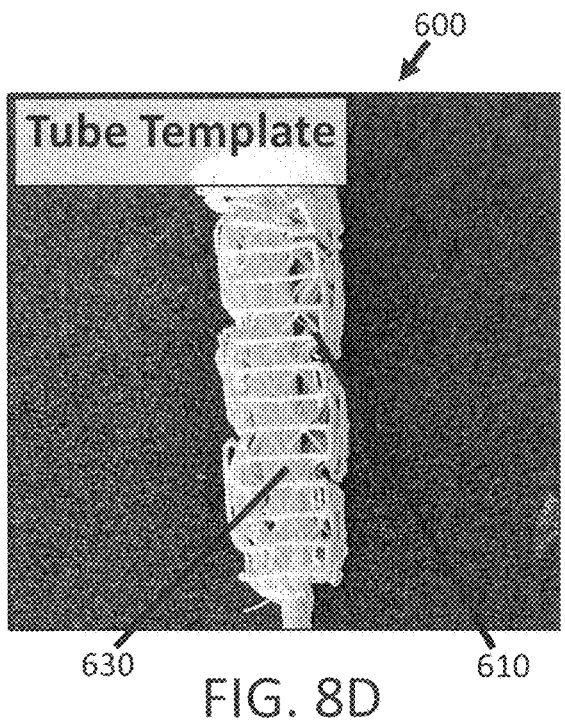
FIG. 8D is a top view of a representative photographic image of a Cell Encapsulation System (CES) in a tube template configuration, in accordance with an example of the disclosure.

FIG. 8D illustrates a tube template configuration of a CES device 600. The tube template configuration is a CES device wherein the injection port 630 additionally operates as the bladder or chamber(s). In comparison to the single lobe configuration of the CES device 100 of FIG. 8A, the tub template configuration is a CES device with an injection port 630 but without a separately defined bladder or chamber(s). The CES device 600 otherwise comprises a sub-cell-scale materially porous solid cell encapsulation membrane (as illustrated FIG. 1B) surrounding the injection port 630, and a supporting scaffold 610 further surrounding the encapsulation membrane and the injection port 630. The tube template configuration may, alternatively, be referred to as a non-lobe configuration. In the example of FIG. 8D, the CES device comprises radial symmetry along its length (i.e., an encapsulating cell tube surrounded by encapsulating membrane and exterior textured scaffold).

As noted by the examples above, the injection port configurations may additionally vary. In some examples, the injection port may be a single port for the entire device such as, for example, the injection port 130 of the CES device 100 of FIG. 8A, the injection port 450 of the CES device 400 of FIG. 8B, and the injection port 530 of the CES device 500 of FIG. 8C. As noted above, a CES device may have multiple injection ports. By example, a CES device may have a single injection port for each lobe. Further yet, a CES device may have multiple injection ports for each lobe. Also, as illustrated by the example of FIG. 8B, the CES device may have a single injection port connected to multiple lobes. Finally, as explained and illustrated by the example of FIG. 8D, the injection port may be the bladder and/or the one or more chambers formed by the cell encapsulation chamber. Also, as described above, a CES device may have one or more injection ports in-plane, or parallel, with the lobe(s). In some in-plane examples, the injection port may traverse the entire length or a substantial length (i.e., more than half) of the lobe (i.e., as illustrated by FIG. 8A), may overlap the entire length of the device (i.e., as also illustrated by FIG. 8A), or may terminate upon entry into the cavity of the lobe at the perimeter of the device (i.e., as illustrated by FIG. 8C). As also described above, a CES device may have one or more injection ports out-of-plane, or non-parallel, with the lobe(s).

Figure 9C:
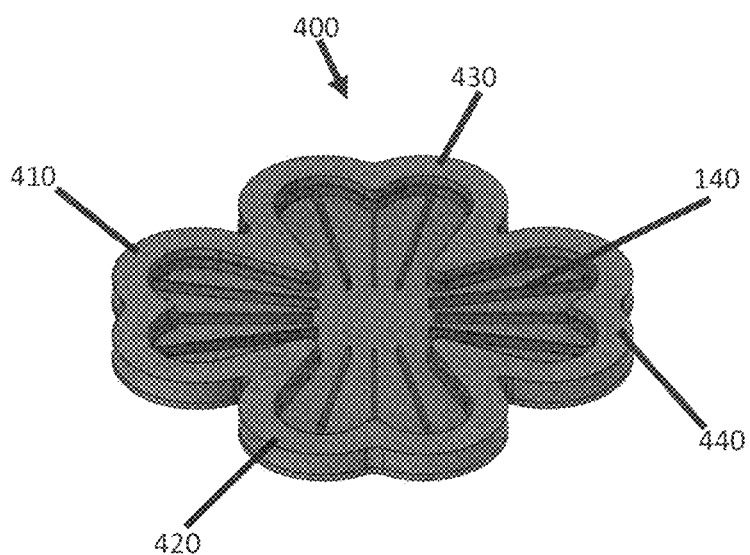
FIG. 9C is another cross-sectional view of a digital representation of a representative example of a Cell Encapsulation System (CES) device in a four-lobe configuration, in accordance with an example of the disclosure.

FIG. 9A is a digital representation of the image of the four-lobe CES device configuration of FIG. 8B. The CES device 400 comprises extensions (or lobes) 410, 420, 430, 440 extending from a central core that is, in this instance, the injection port 450. FIG. 9B is a cross-section of a CES device, bisecting all lobes, such as the CES device 400 of FIG. 9A. As illustrated by FIG. 9B, the lobes may be selectively internally connected (e.g., only two of four lobes in a CES device may be internally connected). Specifically, first lobe 410 and second lobe 420 are internally connected, while third lobe 430 and fourth lobe 440 are isolated from any other lobe of the CES device. In yet another example, FIG. 9C is a cross-section of a CES device, bisecting all lobes, such the CES device 400 of FIG. 9A. As illustrated by FIG. 9C, the CES device 400 may additionally, or alternatively, comprise internal porous supports 140 (as also illustrated by FIG. 1B) in each of a first lobe 410, a second lobe 420, a third lobe 430, and a fourth lobe 440. In the example of FIG. 9C, the lobes are, otherwise, internally connected across the entire device.

Figure 10A:
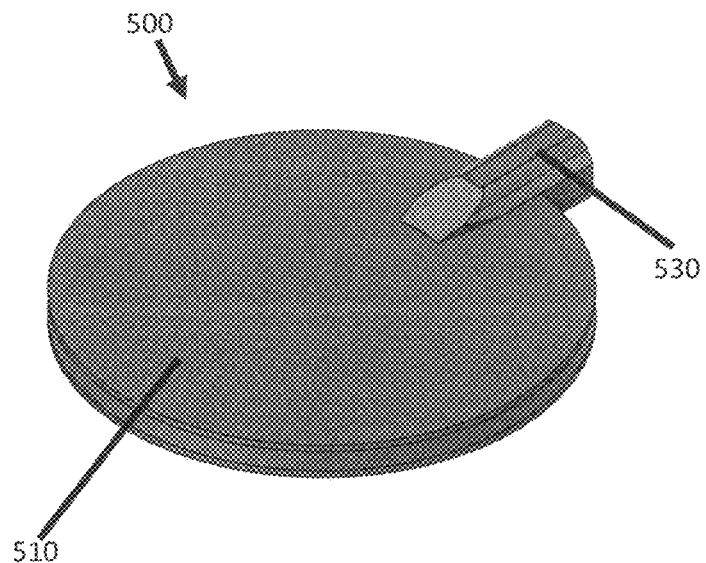
FIG. 10A is a digital representation of a top view of a representative example of a Cell Encapsulation System (CES) device in a donut configuration, in accordance with an example of the disclosure.
Figure 10B:
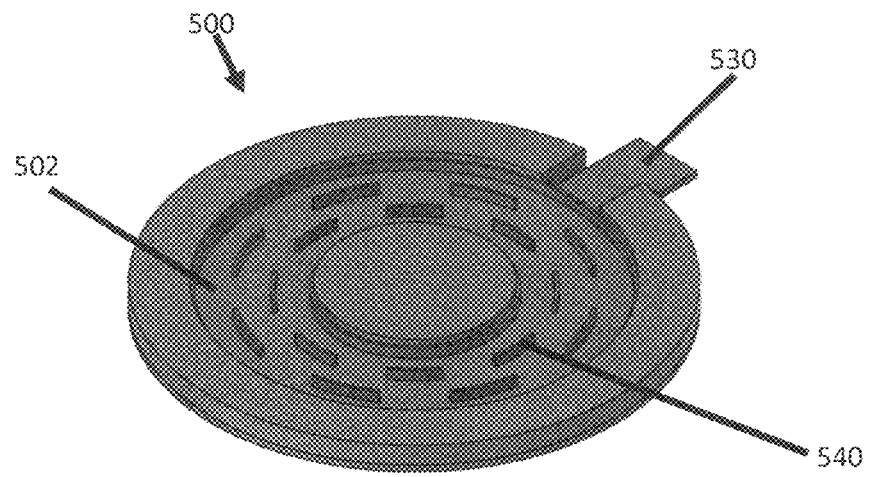
FIG. 10B is a cross-sectional view of a digital representation of a representative example of a Cell Encapsulation System (CES) device in a donut configuration, in accordance with an example of the disclosure.

FIG. 10A is a digital representation of the image of donut CES device configuration of FIG. 8C. The CES device 500 comprises a chamber of a bladder formed by a sub-cell-scale materially porous solid cell encapsulation membrane 510 and an injection port 530. FIG. 10B is a cross-section of a CES device, bisecting the donut, such as the CES device 500 of FIG. 10A. As illustrated by FIG. 10B, the CES device 500 comprises a single chamber 502 with a single access through the injection port 530 provided at its perimeter. The CES device of FIG. 10B further comprises internal porous supports 540 therein.

A variety of configurations of in-plane injections ports 130 are further illustrated by FIGS. 11A-1E. FIG. 11A illustrates an injection port 130 chamfered along three edges 132, 134, 136. FIG. 11B also illustrates a chamfered injection port 130, however, only chamfered at one end 132, with edges 134, 136 at right angles. FIG. 11C illustrates an injection port 130 chamfered at one end 132 with additional edges 134, 136 radiused to form a fillet, or rounded. FIG. 11D illustrates an injection port 130 chamfered at one end 132 with the additional edges 134, 136 chamfered and radiused to form a fillet, or rounded. FIG. 11E illustrates an injection port 130 chamfered with its remaining length curved, or rounded, at a topside 134.

Methods of using the CES device are contemplated herein. One method of use of the CES device includes implantation into a patient with the purpose of treating a variety of possible ailments or conditions. The implanted CES device could contain therapeutically effective amounts of one or more biological factors. Singular or multiple CES devices may be implanted within dermal, sub-dermal, muscle, cartilage, osteochondral, fatty, or composite connective tissues thereof. Singular or multiple CES devices may also be implanted on-top of, immediately adjacent to, or within non-connective tissues and organs, including but not limited to cardiac, kidney, liver, ovarian, testicular, brain, spinal cord, vascular, endocrine, ocular, or other composite tissue. The CES device may be physically implanted and placed using forceps or similar surgical instruments after tissue incision. Alternatively, the CES device may by implanted and placed non-invasively using cannular, catheter, endoscopic, and other minimally invasive surgical techniques. The CES device may be designed to include component regions intended to be used as suture anchors, whereby, upon placement of the CES device at the desired location, the CES device can be mechanically affixed to surrounding tissue and/or separate devices via suture application. Alternatively, the CES device may be fixed to tissue via medical adhesive glues. The CES device may be loaded with cells and sealed prior implantation. Additionally, or alternatively, the CES device, with an extended port that is accessible to loading, may be implanted first and filled with cells at a later time, which may be days, weeks, months, or years. The CES device may consist of multiple ports and/or collections of chambers. In such an example, individual ports may be accessed, and chamber collections filled at different points in time. This may include filling one collection of chambers with one type of cell prior to implantation and filling the other collection(s) of chambers with the same or different types of cells at a later time point. The CES device may also be applied to ex vivo tissues and organs (explanted or engineered) contained within culture and/or bioreactor systems. The CES device may be surgically explanted at any time, including but not limited to at the end of the treatment. The device may be left in the body after treatment termination. The device may alternatively be "deactivated" at treatment termination through the loading of cell-lysing chemistries directly into the device.

Methods of operation of the CES device are also contemplated herein. The general method by which the implanted cell encapsulation system or device operates or functions is as follows. The exterior scaffold portion of the device will rapidly vascularize and integrate with surrounding tissue after implantation. This integration and vascularization mitigates or prevents fibrous encapsulation and acute and chronic local inflammatory response that would otherwise be detrimental to the device function and possibly dangerous to the host patient. The interior cell encapsulation membrane containing the transplanted encapsulated cells prevents native tissue and vasculature from coming into direct contact with the encapsulated cells. The cell encapsulation membrane simultaneously prevents the encapsulated cells from escaping or migrating out of the device. This creates an immune-isolating environment with respect to the transplanted cells, preventing the host tissue from mounting a detrimental local and/or systemic immune response in response to the transplanted encapsulated cells. Transplanted cells may include but are not limited to autologous cells, genetically modified autologous cells, allogeneic cells, genetically modified allogeneic cells, engineered cells, and/or synthetic cells.

In some examples of the CES devices or methods herein, the cell encapsulating walls are thin (<600 micrometers), but highly materially porous, with pore sizes significantly smaller than surrounding native or transplanted encapsulated cells. The transplanted encapsulated cells are able to maintain viability through nutrient and waste diffusion through the materially porous cell encapsulation membrane. Additionally, biomolecular products (e.g., factors) produced by the transplanted encapsulated cells can diffuse through the cell encapsulation membrane and enter the host tissue via vasculature immediately proximal to the exterior surface of the blood (as noted above, the original growth of the vasculature was encouraged by the exterior scaffold portion of the device). This biochemical communication between the host tissue and the transplanted tissue has the added benefit of promoting self-regulation of factor production. For example, elevated signaling molecules in the host tissue may induce increased production of the target factor by the transplanted encapsulated cells. Similarly, reduction of signaling molecules in the host tissue may induce decreased production of the target factor by the transplanted encapsulated cells. This activity may be designed to continue for weeks, months, or years.

In other words, the CES device structure and/or the additional augmenting components that are compatible with the CES device, the CES device's material properties, and the CES device's architectural complexities promote cell diffusion, expansion, maturation, and/or therapeutic effect. The CES device structure and/or the augmenting components promote cellular production (e.g., therapeutic components) and factors in vivo. This production is in response to environmental stimuli (e.g., sense and response). The CES device structure and/or the augmenting components also promote cellular production (e.g., therapeutic components) and factors in vitro (e.g., for collection). This production is in response to environmental stimuli (e.g., sense and response). Further yet, the exterior scaffold of a CES device may be textured and/or static or dynamically seeded with cells different from those within the encapsulation chambers. This further supports the viability and functionality of the encapsulated cells and/or promotes integration with surrounding tissue.

As the CES device is not restricted to carrying one particular cell type, it may be used in conjunction with a single cell line or with multiple different types of cells to treat a variety of local and systemic ailments. The present disclosure thus contemplates methods of treating various ailments and conditions by using the CES device to deliver a therapeutically effective amount of one or more types of cells or other biological factors to a patient in need of such treatment. Some examples of locally relevant treatments include: tumor reduction (through release of onco-specific factors that destroy cancerous cells, or through factors that recruit native immune cells to the tumor site), wound healing (external or internal), tissue repair and regeneration, tissue/organ hyperactivity or hypoactivity correction. Some examples of systemically relevant treatments include hormone production and modulation, oncologic suppressant production (e.g., anti-cancer factors), antibiotic production, antiviral production, anti-inflammatory production, factors that modulate blood pressure, or the like.

The CES device may be loaded with cells or other media, may be sealed, and may be implanted, deployed, or immediately used (e.g., within 1-hour of loading). The CES device may be loaded with cells or other media, may be sealed, and may be cultured for more than 1-hour, 1-day, multiple days, 1-month, or multiple months prior to being implanted, deployed, or used. The CES device may be loaded with cells or other media, may be sealed, and may be cryogenically frozen, before or after additional culture, for storage prior to being implanted, deployed, or used. The CES device may comprise components that are stimulated to induce function. By example, the CES device may comprise cells that actively respond to the chemistry of the local media or tissue. In another example, the CES device may contain augmented compositions that respond to environmental factors, including but not limited to pH, temperature, salinity, enzymatic activity, electrostatics, electrical current, light, biochemical concentration gradients (e.g., glucose gradients).

Figure 13A:
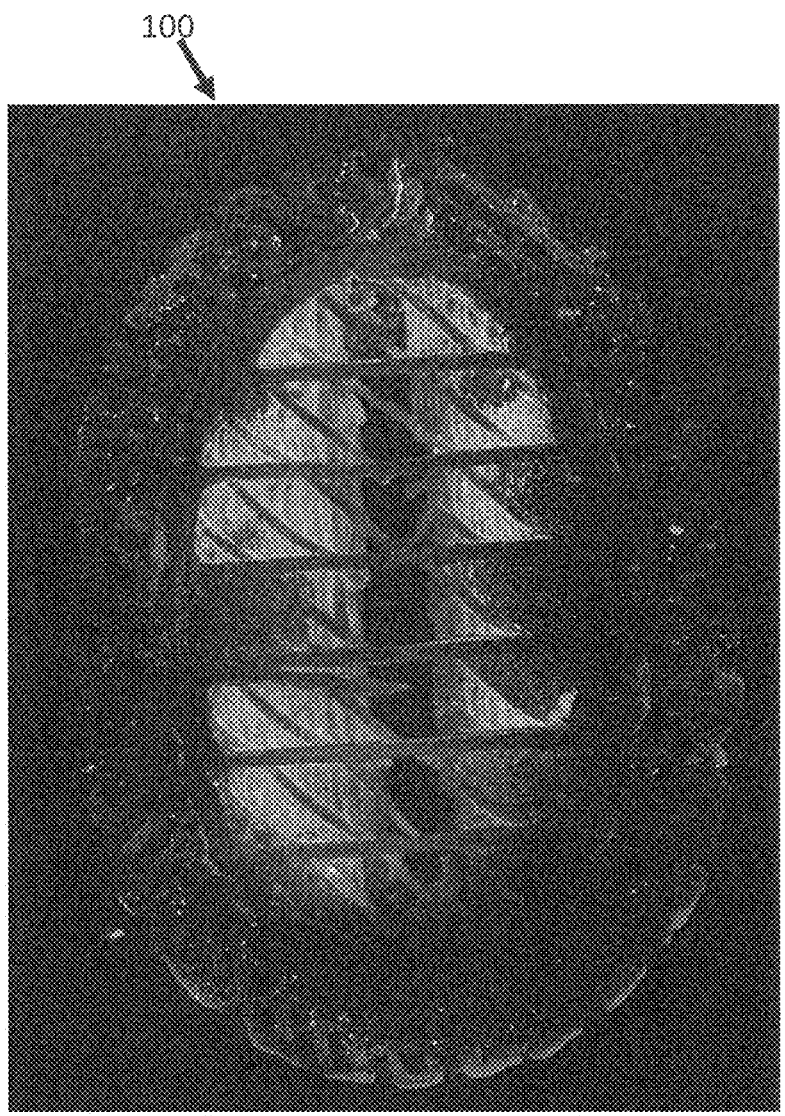
FIG. 13A is a scanning florescent confocal image of a Cell Encapsulation System (CES) device taken seven (7) days after having been loaded with human mesenchymal stem cells and cultured in vitro, in accordance with an example of the disclosure.

FIG. 13A is an image of a CES device 100 scanning florescent confocal. The green of the scan reflects living cells. The red reflects non-living, or dead, materials. By example, the non-living scaffold material of the CES device is additionally reflected in red. The image of the CES device 100 of FIG. 13A were taken seven (7) days after having been loaded with human mesenchymal stem cells and cultured in vitro. This example illustrates that human adherent cells, such as human mesenchymal stem cells survive within the CES device 100 in culture for at least 1-week after loading. FIGS. 14A-14F illustrate a CES device 100 loaded with human HUH7 hepatocytes and cultured in vitro. Like FIG. 13A, in FIGS. 14A-14F, the red reflects non-living, or dead, materials. By example, the non-living scaffold material of the CES device is additionally reflected in red. The CES device 100 of FIGS. 14A-14C is formed of a single porous material (70:70). The single porous material CES device is reflected by the ratio 70:70 where both comprise the same measure of material porosity. The CES device 100 of FIGS. 14D-14F is formed of two materials (62:70). The two-material CES device is reflected by the ratio 62:70 where the membrane is less porous, as reflected by 62, than the scaffold which is more porous, as reflected by 70. As reflected by the margins, FIG. 14A is a scanned image of the CES device 100 of a single material taken after 1-day. FIG. 14B is a scanned image of the CES device 100 of a single material taken after 7-days. FIG. 14A is a scanned image of the CES device 100 of a single material taken after 14 days. FIG. 14A is a scanned image of the CES device 100 of two materials taken after 1-day. FIG. 14A is a scanned image of the CES device 100 of two materials taken after 7-days. FIG. 14A is a scanned image of the CES device 100 of two materials taken after 14-days. These examples illustrate that human non-adherent such as HUH7s can survive within the CES device in culture for at least two weeks after loading. See also FIGS. 15A-15B, 16-16B, and 17 as further described below.

As contemplated by the examples above, the CES device may take any number of final forms or sizes, all of which share key compositional, structural, or manufacturing characteristics, one or more of which may be:

1. Composed of absorbent, biodegradable and/or non-degradable materials.
2. Porous structural exterior comprised of biofriendly materials to promote tissue integration and vascularization.
3. Solid, but nano-micron porosity cell encapsulation membrane within a porous structural exterior.
4. Chambers surrounded by the cell encapsulation membrane to contain the cells.
5. Chamber barriers that are broken upon initial injection or loading.
6. Injection port of the device made from the same or similar material as the device itself that can be mechanically and/or thermally sealed after cell loading.

In examples, The CES device comprises and/or supports one or multiple distinct cell types (autologous, allogeneic, fully engineered, modified autologous, modified allogeneic). In examples, the CES device comprises and/or supports non-adherent cell types. In examples, the CES device comprises and/or supports adherent cell types. In examples, the CES device comprises and/or supports homogeneous population cell aggregates. In examples, the CES device comprises and/or supports heterogeneous population cell aggregates. In examples, the CES device comprises and/or supports autologous or allograft tissue pieces/fragments. In examples, the CES device comprises and/or supports non-cellular particulates, such as nano and/or microparticles. In examples, the CES device is capable of being filled, or loaded, before and/or after implantation. In examples, the CES device is fully-, partially-, and/or non-biodegradable. In examples, the CES device is of one or multiple materials. In examples, the CES device is constructed from one or multiple materials. In examples, the CES device may comprise any combination of features described herein.

As noted above, body fluids from a host (e.g., media, blood, etc.) may additionally absorb into the device upon implantation from a host. This may further promote healthy integration of native host tissue and vasculature with the device exterior and mitigating acute and chronic encapsulation/fibrosis and other non-specific immunological response to the implanted device, while further promoting biochemical exchange/transport between the immunologically isolated, encapsulated cells and the host tissue. In view of these advantages, use for the CES device may include autologous cell loaded devices to treatment of solid tumors, osteoarthritis, liver fibrosis, infarct or otherwise damaged cardiac tissue, neuro/neuromuscular degeneration, central nervous system (spinal cord and brain) damaged and/or degeneration (autologous cells removed from patient and optionally modified—differentiated to other cell types, genetically treated, etc.). The autologous cells may remain contained like described herein but do not necessarily need to be immunologically isolated since they are from the patient receiving the treatment. Cells can be engineered to locally deliver therapeutics to inhibit disease progression, reduce tumor size, reduce tumor reoccurrence, retore tissue, repair tissue, promote tissue growth and/or volumetric tissue expansion, a combination thereof, or the like.

Figure 15A:
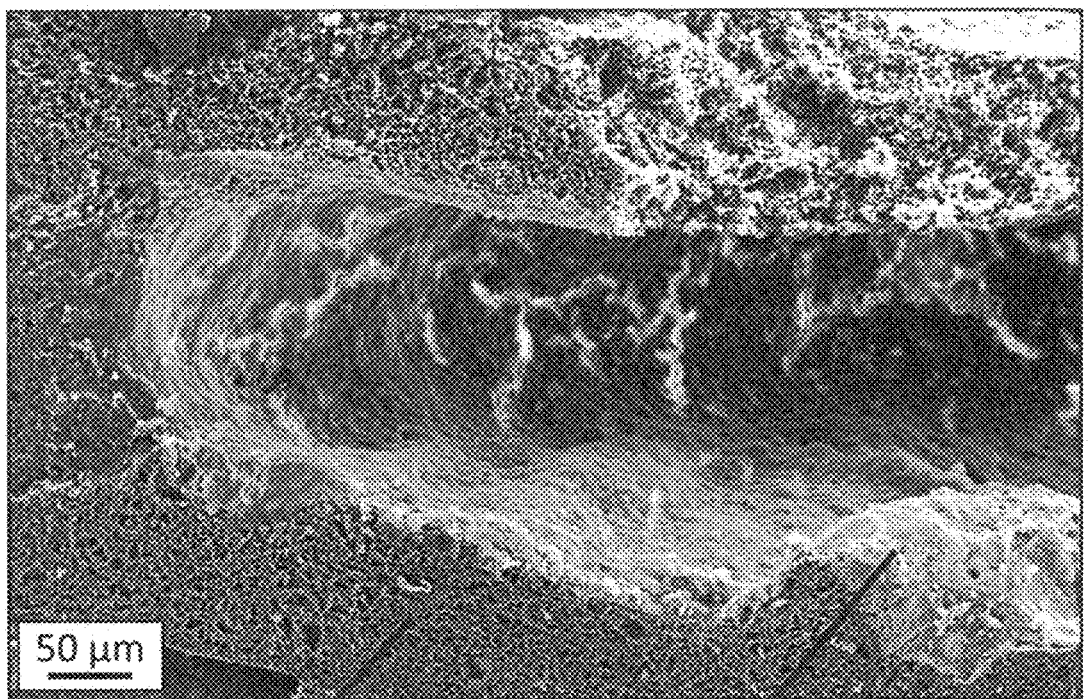
FIGS. 15A-15B are images of selectively colored scanning electron micrographs of interior cross-sections of a Cell Encapsulation System (CES) device taken approximately 30 days after having been loaded and cultured with HUH7 cells, in accordance with an example of the disclosure.
Figure 15B:
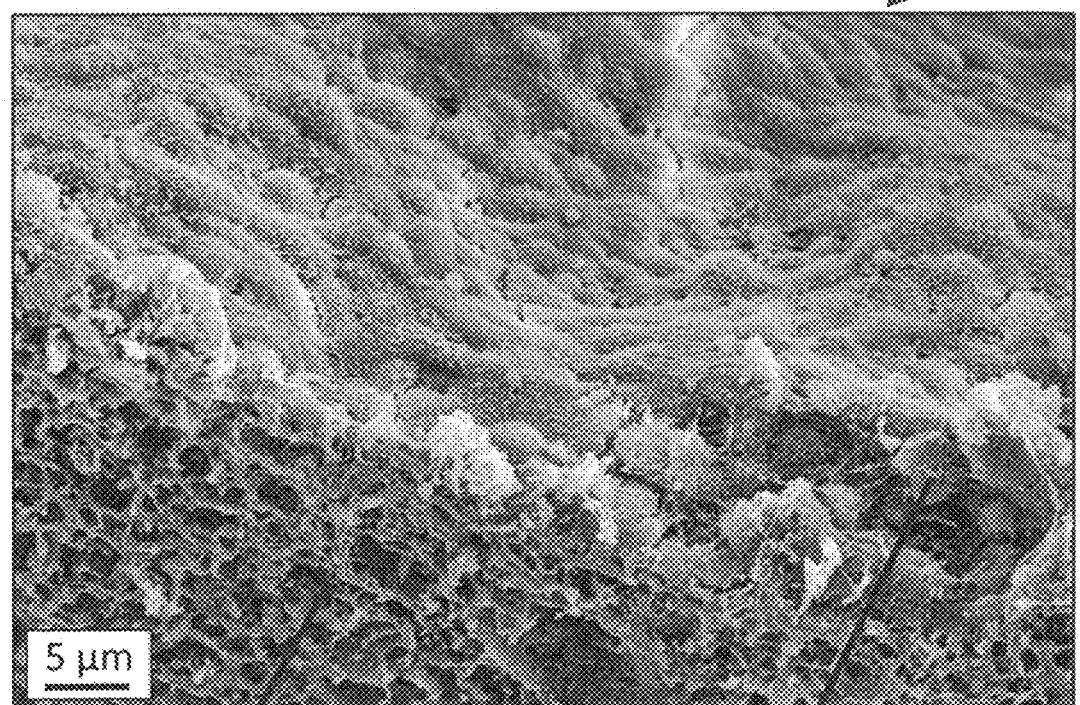
Figure 16:
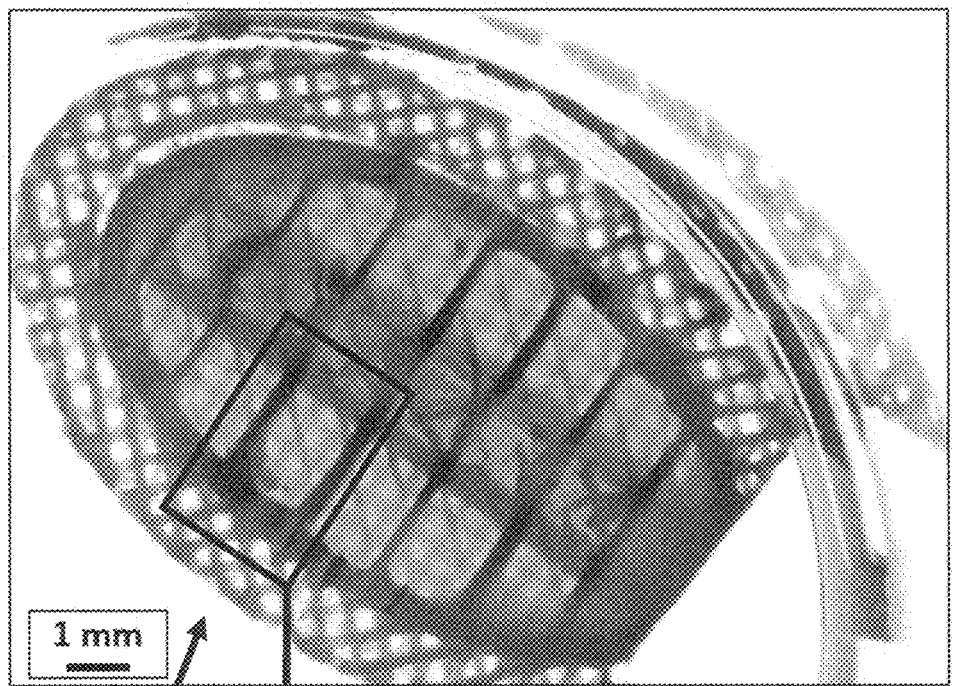
FIG. 16 is a photographic image of a cross-section of a Cell Encapsulation System (CES) device containing primary human islets 9 days after initial loading, in accordance with an example of the disclosure.
Figure 16A:
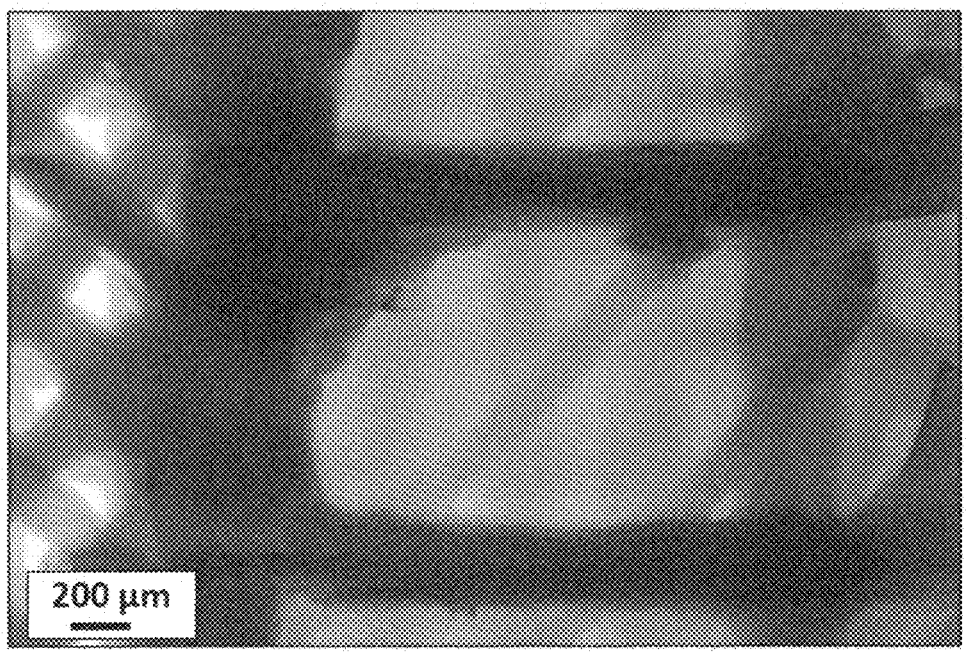
FIG. 16A is a sectional view of the photographic image of FIG. 16 taken at section 16A, in accordance with an example of the disclosure.
Figure 16B:
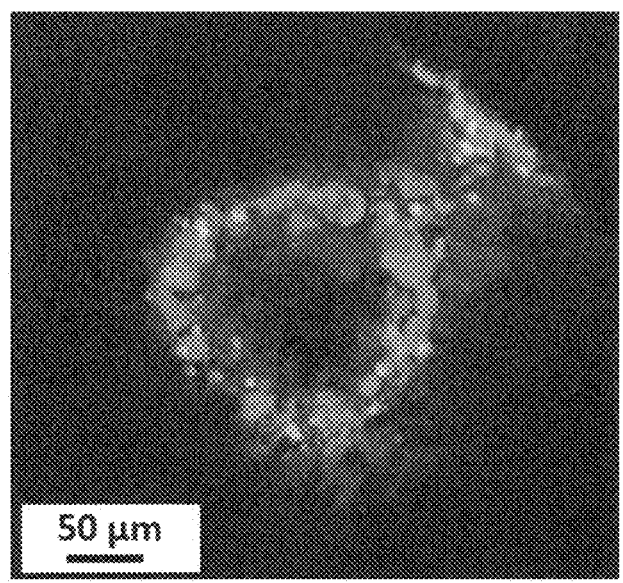
FIG. 16B is a live (green) and dead (red) stained fluorescent scanning confocal microscopic image of a single primary human islet cell cluster with the Cell Encapsulation System (CES) device of FIG. 16, in accordance with an example of the disclosure.
Figure 17:
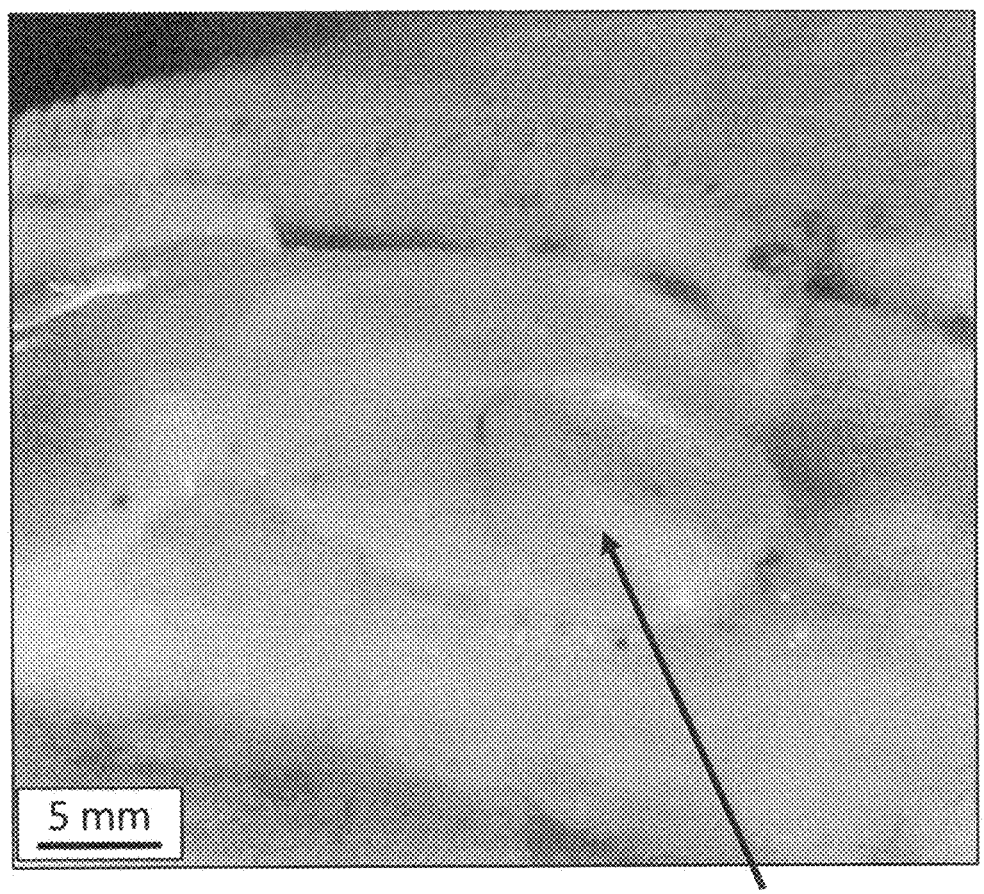
FIG. 17 is a photographic image of a Cell Encapsulation System (CES) device taken six (6) weeks after subcutaneous implantation in a rat and at the time of implant removal, in accordance with an example of the disclosure.

To further illustrate the CES device of the present disclosure additional figures are provided of images of actual devices in various stages of operation and use. FIGS. 15A-15B are scaled images of scanning electron micrographs of an interior cross-section of a CES device 100 of an example of the present disclosure. The images were taken approximately 30 days after being loaded and cultured with HUH7 cells 200. In the images, red reflects the cells 200 and the blue reflects the encapsulating membrane 110. The cells 200 can be seen adhering to and coating interior cell encapsulation membranes 110, which are porous membranes defining the perimeter of the bladder component of the CES device 100. FIG. 16 is a scaled photographic image of a CES device 100 containing primary human islets 9 days after initial loading. FIG. 16A is a scaled image of a sectional view of the photographic image of FIG. 16 taken at section 16A. FIG. 16B is a live (green) and dead (red) stained fluorescent scanning confocal microscopic image of a single primary human islet cell cluster with the CES device of FIG. 16. FIG. 17 is a scaled image of a photograph of the HUH7 loaded CES device 100 taken 6-weeks after subcutaneous implantation into a rat. The photograph of FIG. 17 was taken during implant removal. Vasculatures can be seen on the exterior scaffold portion of the CES device 100.

While this invention has been described with reference to examples thereof, it shall be understood that such description is by way of illustration only and should not be construed as limiting the scope of the claimed examples. Accordingly, the scope and content of the examples are to be defined only by the terms of the following claims. Furthermore, it is understood that the features of any example discussed herein may be combined with one or more features of any one or more examples otherwise discussed or contemplated herein unless otherwise stated.

What is claimed is:

1. A cell encapsulation system comprising:
    a 3D-printed scaffold with scaffold pores formed therein, wherein the material composition of the 3D-printed scaffold comprises biomaterials; and
    a bladder within the 3D-printed scaffold for encapsulating cells, the bladder formed from a materially porous solid cell encapsulation membrane.

2. The cell encapsulation system of claim 1, wherein the bladder encapsulates cells.

3. The cell encapsulation system of claim 1, wherein the 3D-printed scaffold and the materially porous solid cell encapsulation membrane comprise multiple architectures in a single contiguous device.

4. The cell encapsulation system of claim 1, wherein the 3D-printed scaffold is formed through room-temperature based extrusion 3D-printing.

5. The cell encapsulation system of claim 1, wherein the 3D-printed scaffold and the materially porous solid cell encapsulation membrane are formed through room-temperature based extrusion 3D-printing.

6. The cell encapsulation system of claim 1, wherein the 3D-printed scaffold and the materially porous solid cell encapsulation membrane are formed through the same room-temperature based extrusion 3D-printing.

7. The cell encapsulation system of claim 1, wherein a material composition of one or more of the 3D-printed scaffold, the materially porous solid cell encapsulation membrane, combinations thereof, or portions thereof comprises biochemical factors, wherein the biochemical factors comprise one or more of hormones, growth factors, cytokines, peptides, proteins, proteoglycans, enzymes, proteinases, antibiotics, antivirals, antifungals, polysaccharides, opioids, small molecule drugs, and exosomes.

8. The cell encapsulation system of claim 1, wherein a material composition of the materially porous solid cell encapsulation membrane comprises biochemical factors, wherein the biochemical factors comprise one or more of hormones, growth factors, cytokines, peptides, proteins, proteoglycans, enzymes, proteinases, antibiotics, antivirals, antifungals, polysaccharides, opioids, small molecule drugs, and exosomes.

9. The cell encapsulation system of claim 1, wherein the materially porous solid cell encapsulation membrane is nano-micron porous allowing for nutrient, waste and target form factor diffusion while preventing direct interaction of encapsulated cells with host tissue and while the scaffold pores of the 3D-printed scaffold have direct interaction with the host tissue.

10. The cell encapsulation system of claim 1, wherein 3D-printed fibers of the 3D-printed scaffold are stacked with spaces therebetween, the spaces forming the scaffold pores of the 3D-printed scaffold, and 3D-printed fibers of the materially porous solid cell encapsulation membrane are stacked in arrangement with no spacing therebetween.

11. The cell encapsulation system of claim 1, wherein the 3D-printed scaffold or the materially porous solid cell encapsulation membrane are hydrated by fluids after formation or after implantation within a host.

12. The cell encapsulation system of claim 1, wherein the 3D-printed scaffold and the materially porous solid cell encapsulation membrane are embedded with one another.

13. The cell encapsulation system of claim 1, wherein one or more of the 3D-printed scaffold, the materially porous solid cell encapsulation membrane, a combination thereof, or portions thereof are biodegradable.

14. The cell encapsulation system of claim 1, wherein one or more of the 3D-printed scaffold, the materially porous solid cell encapsulation membrane, a combination thereof, or portions thereof are non-biodegradable.

15. The cell encapsulation system of claim 1, wherein one or more of the 3D-printed scaffold, the materially porous solid cell encapsulation membrane, a combination thereof, or portions thereof are a combination of biodegradable and non-biodegradable.

16. The cell encapsulation system of claim 1, wherein the 3D-printed scaffold is biodegradable and the materially porous solid cell encapsulation membrane is non-biodegradable.

17. The cell encapsulation system of claim 1 that is entirely biodegradable.

18. The cell encapsulation system of claim 1 that is entirely non-biodegradable.

19. The cell encapsulation system of claim 1, wherein the bladder comprises a port for inserting cells into the bladder.

20. The cell encapsulation system of claim 19, wherein the bladder comprises internal porous supports perpendicular or oblique to the port and extending across the port.

21. The cell encapsulation system of claim 19, wherein the bladder comprises a plurality of chambers divided by chamber walls wherein each chamber is accessible through the port.

22. The cell encapsulation system of claim 21, wherein the chamber walls are perpendicular to the port.

23. The cell encapsulation system of claim 19, wherein the port is self-sealing.

24. The cell encapsulation system of claim 19, wherein the port is sealed by heating or local melting.

25. The cell encapsulation system of claim 19, wherein the port extends from the 3D-printed scaffold.

26. The cell encapsulation system of claim 19, wherein the port comprises port walls and an internal channel having a greater porosity than the port walls for guiding a needle through one or more chambers.

27. The cell encapsulation system of claim 1, wherein the bladder comprises a single chamber.

28. The cell encapsulation system of claim 1, wherein the bladder formed by the materially porous solid cell encapsulation membrane is fully enclosed within the 3D-printed scaffold.

29. The cell encapsulation system of claim 1, wherein the bladder formed by the materially porous solid cell encapsulation membrane is partially enclosed within the 3D-printed scaffold.

30. The cell encapsulation system of claim 1, wherein cells are encapsulated within the bladder formed by the materially porous solid cell encapsulation membrane and are accompanied by a fluid.

31. The cell encapsulation system of claim 30, wherein the materially porous solid cell encapsulation membrane is translucent to visualize the fluid or the cells within the bladder.

32. A method of forming the cell encapsulation system of claim 1 comprising the steps of:
   3D-printing fibers in an alternating arrangement to form the 3D-printed scaffold with the scaffold pores therein;
   changing a direction of the fibers to 3D-print the fibers in an in-line arrangement with no spacing therebetween to form the materially porous solid cell encapsulation membrane forming the bladder.

33. A method of forming the cell encapsulation system of claim 1 comprising a single forming step for forming the 3D-printed scaffold and the materially porous solid cell encapsulation membrane with numerous architectures.

34. A method of loading the cell encapsulation system of claim 1 comprising the steps of:
   inserting a syringe needle into one or more chambers of the bladder formed by the materially porous solid cell encapsulation membrane;
   injecting a fluid and cells into the bladder formed by the materially porous solid cell encapsulation membrane wherein the materially porous solid cell encapsulation membrane allows diffusion of the fluid into and out of the bladder formed by the materially porous solid cell encapsulation membrane while the cells are maintained within the bladder formed by the materially porous solid cell encapsulation membrane;
   removing the syringe needle from the one or more chambers as the one or more chambers fill;

removing the syringe needle from the bladder formed by the materially porous solid cell encapsulation membrane; and sealing the bladder formed by the materially porous solid cell encapsulation membrane to maintain the cells therein.

35. The method of claim 34, wherein in the step of inserting a needle:

the needle is inserted into a port of the bladder formed by the materially porous solid cell encapsulation membrane, the port having a different architecture than the one or more chambers of the bladder formed by the materially porous solid cell encapsulation membrane and one or more porous supports within the bladder formed by the materially porous solid cell encapsulation membrane wherein the needle is guided by the port and punctures the one or more porous supports within the bladder formed by the materially porous solid cell encapsulation membrane to reach the one or more chambers; and in the step of sealing: the port is pinched to maintain the cells within the bladder formed by the materially porous cell encapsulation membrane.

36. The method of claim 35, wherein in the step of sealing:

the port is further heated or locally melted to maintain the cells therein.

37. A method of implanting the cell encapsulation system of claim 1 comprising the steps of:

implanting one or more of the cell encapsulation systems of claim 1 within dermal, sub-dermal, muscle, cartilage, osteochondral, fatty, or composite connective tissues thereof in a host; or implanting one or more of the cell encapsulation systems of claim 1 on-top of, immediately adjacent to, or within non-connective tissues and organs.

38. The method of claim 37, wherein the non-connective tissues and organs comprise one or more of cardiac, kidney, liver, ovarian, testicular, brain, spinal cord, vascular, endocrine, ocular, or other composite tissue in the host.

39. The method of claim 37, wherein in the step of implanting the one or more cell encapsulation systems of claim 1 the one or more cell encapsulation systems are physically implanted and placed by forceps after a step of tissue incision of the host.

40. The method of claim 37, wherein in the step of implanting the one or more cell encapsulation systems of claim 1 are implanted and placed non-invasively using annular, endoscopic and other minimally invasive surgical techniques.

41. The method of claim 37 further comprising a step of: retaining the one or more cell encapsulation systems of claim 1 within the host after termination of a treatment such that there is no removal of the one or more cell encapsulation systems from the host after implanting.

42. The method of claim 37 further comprising a step of: explanting the one or more cell encapsulation systems of claim 1 from the host to ex vivo tissues or organs contained within a culture or a bioreactor system.

43. The method of claim 37, wherein one or more of the cell encapsulation systems of claim 1 further comprise suture anchors.

44. The method of claim 43 further comprising a step of: mechanically fixing the one or more of the cell encapsulation systems of claim 1 to surrounding tissue via the suture anchors.

45. The method of claim 37 further comprising a step of: affixing the one or more of the cell encapsulation systems of claim 1 to surrounding tissue via adhesive glue.

46. The method of claim 37 further comprising a step of: loading the one or more of the cell encapsulation systems of claim 1 with cells prior to the steps of implanting.

47. The method of claim 37 further comprising a step of: loading the one or more cell encapsulation systems of claim 1 with cells after the steps of implanting.

48. The method of claim 47, wherein the cells loaded prior to the steps of implanting are the same as the cells loaded after the steps of implanting.

49. The method of claim 37 further comprising a step of: loading at least one of the one or more cell encapsulation systems of claim 1 with cells prior to the steps of implanting and loading another one of the one or more of the cell encapsulation systems of claim 1 with cells after the steps of implanting.

50. The method of claim 47, wherein the cells loaded prior to the steps of implanting are different than the cells loaded after the steps of implanting.

51. A method of utilizing the cell encapsulation system of claim 1 comprising the step of:

applying one or more of the cell encapsulation systems of claim 1 to ex vivo tissues or organs contained within a culture or a bioreactor system.

52. The method of claim 51, wherein the ex vivo tissues or organs are explanted.

53. The method of claim 51, wherein the ex vivo tissues or organs are engineered.

54. A method of operating the cell encapsulation system of claim 1 comprising the steps of:

rapidly vascularizing and integrating the 3D-printed scaffold with surrounding tissue of a host after a step of implanting the cell encapsulation system of claim 1 into the host;

preventing native tissue and vasculature from coming into direct contact with encapsulated cells within the bladder formed by the materially porous solid cell encapsulation membrane;

preventing the encapsulated cells within the bladder formed by the materially porous solid cell encapsulation membrane from escaping or migrating from the bladder formed by the materially porous solid cell encapsulation membrane;

maintaining viability of the encapsulated cells through nutrient and waste diffusion through the materially porous solid cell encapsulation membrane; and diffusing biomolecular products produced by the encapsulated cells through the materially porous solid cell encapsulation membrane into the host via vasculature.

55. The method of claim 54 further comprising the step of: self-regulating biomolecular product production by controlling production of target factors of the encapsulated cells based on signaling molecules in the host.

56. The method of claim 55, wherein the encapsulated cells are induced to increase production of the target factors based on the signaling molecules in the host.

57. The method of claim 55, wherein the encapsulated cells are induced to decrease production of the target factors based on the signaling molecules in the host.

58. A method of treating ailments and conditions using the cell encapsulation system of claim 1 comprising the step of:

delivering a therapeutically effective amount of one or more types of cells or other biofactors in the cell encapsulation system to a host in need of such treatment.

* * * * *